US012582599B2

(12) United States Patent
Giesing et al.

(10) Patent No.: US 12,582,599 B2
(45) Date of Patent: Mar. 24, 2026

(54) METHODS FOR TREATMENT OF BLADDER CANCER WITH GEMCITABINE

(71) Applicant: TARIS Biomedical LLC, Lexington, MA (US)

(72) Inventors: Dennis Giesing, Lee's Summit, MO (US); Heejin Lee, Bedford, MA (US); Karen Daniel, Newton, MA (US)

(73) Assignee: TARIS Biomedical LLC, Lexington, MA (US)

( * ) Notice: Subject to any disclaimer, the term of this patent is extended or adjusted under 35 U.S.C. 154(b) by 0 days.

(21) Appl. No.: 17/811,296

(22) Filed: Jul. 7, 2022

(65) Prior Publication Data

US 2022/0347091 A1     Nov. 3, 2022

Related U.S. Application Data

(63) Continuation of application No. 17/561,540, filed on Dec. 23, 2021, now abandoned, which is a continuation of application No. 14/641,009, filed on Mar. 6, 2015, now abandoned.

(60) Provisional application No. 61/949,215, filed on Mar. 6, 2014.

(51) Int. Cl.
| | |
|---|---|
| *A61K 9/00* | (2006.01) |
| *A61K 31/7068* | (2006.01) |
| *A61K 45/06* | (2006.01) |
| *A61M 31/00* | (2006.01) |
| *A61P 13/10* | (2006.01) |
| *A61P 35/00* | (2006.01) |
| *C07H 19/06* | (2006.01) |

(52) U.S. Cl.
CPC .......... *A61K 9/0034* (2013.01); *A61K 9/0004* (2013.01); *A61K 9/0024* (2013.01); *A61K 9/0092* (2013.01); *A61K 31/7068* (2013.01); *A61K 45/06* (2013.01); *A61M 31/002* (2013.01); *A61P 13/10* (2018.01); *A61P 35/00* (2018.01); *C07H 19/06* (2013.01)

(58) Field of Classification Search
None
See application file for complete search history.

(56) References Cited

U.S. PATENT DOCUMENTS

| | | | |
|---|---|---|---|
| 4,008,719 A | | 2/1977 | Theeuwes et al. |
| 4,111,203 A | * | 9/1978 | Theeuwes ............ A61K 9/0004 424/431 |
| 6,171,298 B1 | | 1/2001 | Masuura et al. |
| 8,343,516 B2 | | 1/2013 | Daniel et al. |
| 8,679,094 B2 | | 3/2014 | Cima et al. |
| 8,690,840 B2 | | 4/2014 | Lee et al. |
| 8,721,621 B2 | | 5/2014 | Boyko et al. |
| 8,801,694 B2 | | 8/2014 | Lee et al. |
| 9,017,312 B2 | | 4/2015 | Lee et al. |
| 9,107,816 B2 | | 8/2015 | Lee et al. |
| 9,457,176 B2 | | 10/2016 | Lee et al. |
| 9,539,303 B2 | | 1/2017 | McCulloch et al. |
| 9,586,035 B2 | | 3/2017 | Cima et al. |
| 9,636,488 B2 | | 5/2017 | Giesing |
| 10,543,346 B2 | | 1/2020 | Giesing |
| 10,792,297 B2 | | 10/2020 | Giesing et al. |
| 10,857,173 B2 | | 12/2020 | Giesing |
| 11,446,322 B2 | | 9/2022 | Giesing |
| 2004/0106914 A1 | | 6/2004 | Coppeta et al. |
| 2004/0260272 A1 | | 12/2004 | Friedman et al. |
| 2005/0070884 A1 | * | 3/2005 | Dionne ................ A61K 9/0004 604/892.1 |
| 2006/0057208 A1 | * | 3/2006 | Holzer ............... A61K 31/7068 424/234.1 |
| 2007/0202151 A1 | | 8/2007 | Lee et al. |
| 2008/0221557 A1 | | 9/2008 | Santini |
| 2009/0149833 A1 | | 6/2009 | Cima et al. |
| 2009/0305956 A1 | | 12/2009 | McCulloch |
| 2010/0003297 A1 | | 1/2010 | Tobias et al. |
| 2010/0015200 A1 | | 1/2010 | McClain et al. |
| 2010/0330149 A1 | | 12/2010 | Daniel et al. |
| 2010/0331770 A1 | | 12/2010 | Lee et al. |

(Continued)

FOREIGN PATENT DOCUMENTS

| | | |
|---|---|---|
| EP | 1913962 A1 | 4/2008 |
| RU | 2591946 C2 | 4/2016 |

(Continued)

OTHER PUBLICATIONS

Laquente; "Antiangiogenic effect of gemcitabine follownig metronomic administration in a pancrease cancer model," 2008; American Assn. Cancer, Molecular Cancer Therapeutics, vol. 7, No. 3, pp. 638-647. (Year: 2008).*
Shelly; "Intravesical gemcitabine therapy for non-mucle invasive bladder cancer (NMIBC): a systemic review," 2012; BJU International; Cochrane Review, vol. 109, pp. 496-505. (Year: 2012).*
Merck Index entry for gemcitabine (M5690); p. 1. (Year: 2013).*
Hertel et al.; "Synthesis and Biological Activity of 2',2'-Difluorodeoxycytidine (Gemcitabine),"—Ojima et al.; Biomedical Frontiers of Fluorine Chemistry, Chapter 19, pp. 265-278 (ACS Symposium Series, vol. 639, 1996). (Year: 1996).*

(Continued)

*Primary Examiner* — David J Blanchard
*Assistant Examiner* — Ivan A Greene
(74) *Attorney, Agent, or Firm* — Morrison & Foerster LLP

(57) ABSTRACT

Drug delivery devices and methods are provided for administering gemcitabine to a patient in need of treatment of bladder cancer by intravesically administering gemcitabine into the bladder of the patient to achieve a sustained concentration of the gemcitabine in urine in the bladder sufficient to produce a therapeutically effective concentration of the gemcitabine in the tissues of the bladder. In embodiments, the local administration into the patient's bladder is at a mean average amount of from 1 mg/day to about 300 mg/day of the gemcitabine (FBE).

5 Claims, 14 Drawing Sheets

(56)            References Cited

U.S. PATENT DOCUMENTS

| 2011/0060309 | A1* | 3/2011 | Lee | A61K 9/0092 |
| | | | | 514/626 |
| 2011/0152839 | A1* | 6/2011 | Cima | A61L 31/16 |
| | | | | 604/93.01 |
| 2011/0202036 | A1 | 8/2011 | Boyko et al. | |
| 2011/0218488 | A1 | 9/2011 | Boyko et al. | |
| 2012/0089122 | A1 | 4/2012 | Lee et al. | |
| 2012/0157917 | A1 | 6/2012 | Schroeder | |
| 2012/0203203 | A1 | 8/2012 | Lee et al. | |
| 2013/0046275 | A1 | 2/2013 | Holzer et al. | |
| 2013/0158675 | A1 | 6/2013 | Hutchins et al. | |
| 2013/0324946 | A1 | 12/2013 | Tobias et al. | |
| 2014/0056986 | A1 | 2/2014 | Desai | |
| 2014/0221981 | A1 | 8/2014 | Cima | |
| 2014/0276636 | A1 | 9/2014 | Lee et al. | |
| 2014/0308336 | A1 | 10/2014 | Indolfi et al. | |
| 2015/0005595 | A1 | 1/2015 | Tepper et al. | |
| 2015/0165177 | A1 | 6/2015 | Giesing | |
| 2015/0165178 | A1 | 6/2015 | Giesing | |
| 2015/0182516 | A1 | 7/2015 | Giesing | |
| 2015/0216937 | A1 | 8/2015 | Wen | |
| 2015/0250717 | A1 | 9/2015 | Giesing | |
| 2015/0313856 | A1 | 11/2015 | Gagnon et al. | |
| 2015/0360012 | A1 | 12/2015 | Sansone | |
| 2016/0008271 | A1 | 1/2016 | Lee | |
| 2016/0199544 | A1 | 7/2016 | Lee et al. | |
| 2016/0310715 | A1 | 10/2016 | Lee | |
| 2017/0157360 | A1 | 6/2017 | Cima | |
| 2019/0060344 | A1 | 2/2019 | Giesing | |
| 2019/0175637 | A1 | 6/2019 | Giesing | |
| 2019/0388338 | A1 | 12/2019 | Giesing | |
| 2020/0060966 | A1 | 2/2020 | Giesing | |
| 2021/0085705 | A1 | 3/2021 | Giesing et al. | |
| 2021/0145856 | A1 | 5/2021 | Giesing | |
| 2022/0117886 | A1 | 4/2022 | Giesing et al. | |
| 2023/0075819 | A1 | 3/2023 | Giesing | |
| 2023/0321129 | A1 | 10/2023 | Giesing et al. | |

FOREIGN PATENT DOCUMENTS

| WO | 2006030431 | A2 | 3/2006 |
| WO | 2009139984 | A2 | 11/2009 |
| WO | 2010151893 | A1 | 12/2010 |
| WO | 2011031855 | A2 | 3/2011 |
| WO | 2011089604 | A2 | 7/2011 |
| WO | 2012048114 | A1 | 4/2012 |
| WO | 2012096985 | A1 | 7/2012 |
| WO | 2012106714 | A1 | 9/2012 |
| WO | 2013148337 | A1 | 10/2013 |
| WO | 2013170069 | A1 | 11/2013 |
| WO | 2014036555 | A1 | 3/2014 |
| WO | 2014036556 | A2 | 3/2014 |
| WO | 2014144066 | A1 | 9/2014 |
| WO | 2014145638 | A1 | 9/2014 |
| WO | 2015026813 | A1 | 2/2015 |
| WO | 2015069723 | A1 | 5/2015 |
| WO | 2015134911 | A1 | 9/2015 |
| WO | 2015200752 | A1 | 12/2015 |
| WO | 2017193098 | A1 | 11/2017 |
| WO | 2019023388 | A1 | 1/2019 |
| WO | 2019094517 | A1 | 5/2019 |
| WO | 2020028554 | A1 | 2/2020 |

OTHER PUBLICATIONS

Gontero et al.; "The Impact of Intravesical Gemcitabine and 1/3 Dose Bacillus Calmette-Guerin Instillation Therapy on the Quality of Life in Patients with Nonmuscle Invasive Bladder Cancer: Results of a Prospective, Randomized, Phase II Trial," The Journal of Urology, vol. 190, pp. 857-862. (Year: 2013).*

Giannantoni et al.; "New Frontiers in Intravesical Therapies and Drug Delivery," 2006; European Assn. of Urology; European Urology, vol. 50, pp. 1183-1193. (Year: 2006).*

Merck Index entry for lidocaine (M6805), pp. 1-2. (Year: 2013).*

Khaled; "Primary chemotherapy with low-dose prolonged infusion gemcitabine and cisplatin in patients with bladder cancer: A Phase II trial," 2008; Elsevier, Urologic Oncology: Seminars and Investigations, vol. 26, pp. 133-136. (Year: 2008).*

Mendelsohn et al.; "Bladder cancers arise from distinct urothelial sub-populations," 2014, NPG; Nature Cell Biology, vol. 16, No. 10, pp. 982-991 and S1-S5 (16-pages). (Year: 2014).*

Banerjee; "Intravesical drug delivery: Challenges, current status, opportunities and novel strategies," 2010, Elsevier; Journal of Controlled Release, vol. 148, pp. 147-159. (Year: 2010).*

Frea; "Intravesical gemcitabine for superficial bladder cancer: rationale for a new treatment option," 2005, BJU international, vol. 96, No. 7, pp. 970-976. (Year: 2005).*

Khaled; "Primary chemotherapy with low-dose prolonged infusion gemcitabine and cisplatin in patients with bladder cancer: A Phase II trial," 2008; Elsevier, Urologic Oncology: Seminars and Investigations, vol. 26, pp. 133-136. (Year: 2006).*

Laquente; "Antiangiogenic effect of gemcitabine following metronomic administration in a pancreas cancer model," 2008; American Assn. Cancer, Molecular Cancer Therapeutics, vol. 7, No. 3, pp. 638-647. (Year: 2008).*

Shelly; "Intravesical gemcitabine therapy for non-muscle invasive bladder cancer (NMIBC): a systemic review," 2012; BJU International; Cochrane Review, vol. 109, pp. 496-505. (Year: 2012).*

Mattioli et al.; "Intravesical Gemcitabine in Superficial Bladder Cancer: a Phase II Safety, Efficacy and Pharmacokinetic Study," 2005; International Institute of Anticancer Research; Anticancer Research, vol. 25, pp. 2493-2496. (Year: 2005).*

Daneshmand et al.; "The safety, tolerability, and efficacy of a neoadjuvant gemcitabine intravesical drug delivery system (TAR-200) n muscle-invasive bladder cancer patients: a phase I trial," 2022, Elsevier, Urologic Oncology: Seminars and Original Investigations, vol. 40, pp. 344.e1-344.e9. (Year: 2022).*

Daneshmand et al.; "Development of TAR-200: A novel targeted releasing system designed to provide sustained delivery of gemcitabine for patients with bladder cancer," 2025, Elseivier, Urologic Oncology: Seminars and Original Investigations, vol. 43, pp. 286-296, plus "Supplementary Material" pp. 1-12. (Year: 2025).*

Daneshmand et al.; "TAR-200 for Bacillus Calmette-Guerin-Unresponsive High-Risk Non-Muscle-Invasive Bladder Cancer: Results From the Phase IIb SunRISe-1 Study," 2025, ASCO; Journal of Clinical Oncology, vol. 43, No. 33, pp. 3578-3888. (Year: 2025).*

AUA Treatment Guidelines https://www.auanet.org/guidelines/bladder-cancer-non-metastatic-muscle-invasive-(2017), pp. 1-62.

Bellmunt et al. (Aug. 2003). "New Drugs and New Approaches in Metastatic Bladder Cancer," Crit. Rev. Oncol. Hematol. 47(2):195-206.

Cattel et al., "Pharmacokinetic Evaluation of Gemcitabine and 2',2'-Difluorodeoxycytidine-5'-Triphosphate after Prolonged Infusion in Patients Affected by Different Solid Tumors," Annals of Oncology, 2006, 17(5): pp. 142-147.

Cho et al., "The Effects of Intravesical Chemoimmunotherapy with Gemcitabine and Bacillus Calmette-Guerin in Superficial Bladder Cancer: A Preliminary Study," Journal of Int'l Medicine Research, 2009, 37, pp. 1823-1830.

Cronauer et al., "Inhibitory Effects of the Nucleotide Analogue Gemcitabine on Prostatic Carcinoma Cells," Prostate, 1996, 28, pp. 172-181.

FDA Grants Fast Track Designation for TAR-200 in Muscle-Invasive Bladder Cancer, The Asco Post, posted Apr. 6, 2018, 1-page.

FDA: Number of fast track designation requests granted, https://www.accessdata.fda.gov/scripts/fdatrack/view/track.cfm?program=cder&status=public&id=CDER-RRDS-Number-of-Fast-Track-Designations . . . , accessed May 1, 2019, pp. 1-3.

Fast Track, Breakthrough Therapy, Accelerated Approval, and Priority Review>Fast Track, https://web.archive.org/web/20190423030711/https://www.fda.gov/ForPatients/Approvals/Fast/ucm405399.htm, accessed May 1, 2019, pp. 1-2.

(56)         References Cited

OTHER PUBLICATIONS

Gontero et al. (2005). "Intravesical Gemcitabine For Superficial Bladder Cancer: Rationale For a New Treatment Option," BJU International 96: 970-976.

Guhasarkar S. et al. "Intravesical Drug Delivery: Challenges, Current Status, Opportunities, and Novel Strategies," J. Control Release, 2010, 148(2): pp. 147-159.

Hendricksen et al., "Intravesical Gemcitabine: An Updated of Clinical Results," Lippincott Williams & Wilkins, Curr. Opin. Urol., 2006, 16: pp. 361-366.

Horinaga et al., "Enhanced Antitumor Effect of Coincident Intravesical Gemcitabine Plus BCG Therapy in an Orthotopic Bladder Cancer Model," Urology, 2010, 76(5):1267.e1-1267.e6.

Jantscheff et al., "Liposomal Gemcitabine (GemLip)-Efficient Drug Against Hormone-Refractory Dul45 and PC-3 Prostate Cancer Xenografts," The Prostate, 2009 69: pp. 1151-1163.

Jeon et al., "Induction of Caspase Mediate Apoptosis and Down-Regulation of Nuclear Factory-[kappa]B and Akt Signaling are Involved in the Synergistic Antitumor Effect of Gemcitabine and the Histone Deacetylase Inhibitor Trichostatin A in Human Bladder Caner Cells," The Journal of Urology, 2011, 186(5): pp. 2084-2093.

Kamat et al. "Definitions, End Points, and Clinical Trial Designs for Non-Muscle-Invasive Bladder Cancer: Recommendations From the International Bladder Cancer Group," Journal of Clinical Oncology, 2016, 34(16): pp. 1935-1944.

Khaled et al., "Primary chemotherapy with low-dose prolonged infusion gemcitabine and cisplatin in patients with baldder cancer: A Phase II trial," Urologic Oncology: Seminars and Investigations, 2008, 26:2, pp. 133-136.

Kharkevich, D.A. (2010). Pharmacologia, 10th Edition M., Geotar-Media, p. 73-74, English Translation, 4 pages.

Laquente et al., "Antiangiogenic effect of gemcitabine following metronomic administration in a pancreas cancer model," Molecular Cancer Therapeutics, 2008, 7(3): pp. 638-647.

Laufer et al., "Intravesical Gemcitabine Therapy for Superficial Transitional Cell Carcinoma of the Bladder: A Phase I and Pharmacokinetic Study," J. Clin. Oncol., 2003, 21(4): pp. 697.703.

Lein et al., "Low-dose metronomic chemotherapy: A systemic literature analysis," European Journal of Cancer, 2013, 49: pp. 3387-3395.

Merriam-Webster "Merriam-Webster's Collegiate Dictionary, 11th edition," 2003; Merriam-Websters Inc; entry for "derivative," pp. 67, 85, and 768-769. (Year: 2004).

Messing et al., "Effect of Intravesical Instillation of Gemcitabine vs Saline Immediately Following Resection of Suspected Low-Grade Non-Muscle-Invasive Bladder Cancer on Tumor Recurrence," JAMA, 2018, 319(18): pp. 1880-1888.

Mini et al. "Cellular Pharmacology of Gemcitabine," Annals of Oncology, 2006, 17(5): v7-v12.

Morant et al., "Response and Palliation in a Phase II Trial of Gemcitabine in Hormone-Refractory Metastatic Prostatic Carcinoma," Annals of Oncology, 2000, 11: pp. 183-188.

Muenchen et al., "The Study of Gemcitabine in Combination with Other Chemotherapeutic Agents as an Effective Treatment for Prostate Cancer," Anticancer Research, 2000, 20(2): pp. 735-740.

Nativ et al., "Antineoplastic Effect of Gemcitabine in an Animal Model of Superficial Bladder Cancer," Urology, 2004, 64(4): pp. 845-848.

PCT International Search Report and Written Opinion for PCT Application No. PCT/US2013/057841 mailed Feb. 14, 2014 (18 pages).

PCT International Search Report and Written Opinion for PCT Application No. PCT/US2015/019262 mailed May 22, 2015 (15 pages).

Reagan-Shaw et al. "A Dose Translation From Animal To Human Studies Revisited," The FASEB Journal, 2008, 22: pp. 659-661.

Sasaki et al. "Non-Muscle Invasive Bladder Cancer With Multiple Bone Metastasis Without Local Invasion," Hinyokika Kiyo, 2013, 59(10): pp. 669-672.

Schlack et al. "The Safety and Efficacy of Gemcitabine for The Treatment of Bladder Cancer," Expert Rev. Anticancer Ther., 2016, 16(3): pp. 255-271.

Shelley et al., "Intravesical Gemcitabine Therapy for Non-Muscle Invasive Bladder Cancer (NMIBC): A Systematic Review," BJU Int'l, 2012, 109(4): pp. 496-505.

Singapore Search Report of Application No. 11201591482X dated Oct. 28, 2015, pp. 1-3.

Skinner et al. "SWOG S0353: Phase II trial of intravesical gemcitabine in patients with nonmuscle invasive bladder cancer and recurrence after 2 prior courses of intravesical bacillus Calmette-Guerin," The Journal of Urology, 2013, 190(4): pp. 1200-1204.

Sugiyama et al., "Pharmacokinetics of Gemcitabine in Japanese Cancer Patients: The Impact of a Cytidine Deaminase Polymorphism," Journal of Clinical Oncology, 2007, 25(1): pp. 32-42.

Veltkamp et al., "Oral Administration of Gemcitabine in Patients with Refractory Tumors: A Clinical and Pharmacologic Study," Clinical Cancer Res., 2008, 14(11): pp. 3447-3486.

Xinwu et al., "Effect of Intravesical Instillatoin Capecitabine Combined with Oxaliplatin on the Recurrence of Bladder Cancer," Anti-Tumor Pharmacy, 2011, 1(3): pp. 203-205.

Zhulenko, V.N. et al. (2008). Pharmacologia M., KolosS, 34-35, English Translation, 4 pages.

Zlotta, "The management of MCG failure in non-muscle-invasive bladder cancer: an update," Can Urol Assoc J., 2009, 3(Suppl 4): pp. S199-S205.

Campodonico, et al. "Intravesical Gemcitabine in Recurrent Superficial Bladder Carcinoma: Preliminary Results on Ablative Efficacy and Tolerability," Anticancer Research, May 2005, vol. 25 pp. 2381-2384 (2005).

Anandadas, C. et al. (Dec. 31, 2013). "Bladder Preservation by Neoadjuvant Chemotherapy Followed by Concurrent Chemoradiotherapy With Gemicitabine in Muscle Invasive Bladder Cancer MIBC," Clinical Oncology 25: e67-e74, 1 page.

Anonymous (2019). Fast Track, Breakthrough Therapy, Accelerated Approval, and Priority Review Fast Track, retrieved from the Internet: https:/web_archive_org/web/20190423030711/https:/www. fda.gov/ForPatients/Approvals/Fast/ucm405399_htm, accessed May 1, 2019, 2 pages.

Anonymous (2023). FDA: Number of Fast Track Designation Requests Granted, retrieved from the Internet: https://www.fda.gov/ about-fda/center-biologics-evaluation-and-research-cber/fast-track-designation-request-performance, accessed Mar. 23, 2023, 1 page.

Anonymous (Apr. 6, 2018). "FDA Grants Fast Track Designation for TAR-200 in Muscle-Invasive Bladder Cancer," ASCO Post, 3 pages.

Anonymous (Jan. 6, 2017). "TARIS Biomedical Announces Positive Results from Ph1b Trial of TAR-200 (GemRIS™) in Patients with Muscle Invasive Bladder Cancer," retrieved from the Internet: www.businesswire.com/news/home/20170106005117/en/TARIS-Biomedical-Announces-Positive-Results-Phlb-Trial, last visited Nov. 11, 2019, 3 pages.

Atasoy, B.M. et al. (2014, e-pub. Apr. 25, 2013). "Concurrent Chemoradiotherapy With Low Dose Weekly Gemcitabine In Medically Inoperable Muscle-Invasive Bladder Cancer Patients," Clin. Transl. Oneal. 16:91-95.

Bellmunt, J. et al. (Aug. 2003). "New Drugs and New Approaches in Metastatic Bladder Cancer," Crit. Rev. Oncol. Hematol. 47(2):195-206.

Bidnur, S. et al. (Jan. 7, 2016). "Inhibiting Immune Checkpoints for the Treatment of Bladder Cancer," Bladder Cancer 2(1):15-25.

Borut, K. et al. (2012, e-pub. Sep. 2, 2011). "Phase I Study of Radiochemotherapy With Gemcitabine in Invasive Bladder Cancer," Radiotherapy and Oncology 102:412-415.

Breyer, B.N. et al. (2010). "Sequential Intravesical Gemcitabine and Mitomycin C Chemotherapy Regimen in Patients With Non-Muscle Invasive Bladder Cancer," Urol. Oncol. 28(5):510-514, 9 pages.

Caffo, O. et al. (Oct. 22, 2012). "Trimodality Treatment in the Conservative Management of Infiltrating Bladder Cancer: A Critical Review of the Literature," Critical Reviews in Oncology/Hematology 86(2):176-190.

Cattel, L. et al. (2006). "Pharmacokinetic Evaluation of Gemcitabine and 2',2'-Difluorodeoxycytidine-5'-Triphosphate after Prolonged Infu-

(56) References Cited

OTHER PUBLICATIONS sion in Patients Affected by Different Solid Tumors," Annals of Oncology 17(Suppl. 5):v142-v147.

Chang, S.S. et al. (2017). "Treatment of Non-Metastatic Muscle-Invasive Bladder Cancer: AUA/ASCO/ASTRO/SUO Guidelines," American Urological Association, 62 pages.

Chauvet, B. et al. (Oct. 31, 1996). "Concurrent Cisplatin and Radiotherapy For Patients With Muscle Invasive Bladder Cancer Who Are Not Candidates For Radical Cystectomy," The Journal of Urology 156(4):1258-1262. Abstract Only.

Cho, D.Y. et al. (2009). "The Effects of Intravesical Chemoimmunotherapy with Gemcitabine and Bacillus Calmette-Guerin in Superficial Bladder Cancer: A Preliminary Study," The Journal of International Medical Research 37:1823-1830.

clinicaltrial.gov NCT03518320 (May 8, 2018). "Safety and Tolerability of TAR-200 and Nivolumab in Subjects with Muscle-Invasive Bladder Cancer," retrieved from the Internet https://clinicaltrials.gov/ct2/show/NCT03518320, last visited Oct. 27, 2022, 11 pages.

clinicaltrials.gov. NCT02720367. (Mar. 21, 2016; updated Apr. 19, 2018). "Safety and Tolerability of TAR-200 mg in Subjects With Non-Muscle-Invasive Bladder Cancer," located at https://clinicaltrials.gov/ct2/history/NCT02720367?A=6&B=6&C=merged, last visited on Feb. 21, 2019, 14 pages.

clinicaltrials.gov. NCT02722538. (Apr. 19, 2016). "Safety and Tolerability of GemRIS 225 mg in Subjects With Muscle-Invasive Bladder Cancer," located at https://clinicaltrials.gov/ct2/history/NCT02722538?V_2=View#StudyPageTop, last visited on Jan. 30, 2022, 5 pages.

clinicaltrials.gov. NCT02722538. (Mar. 30, 2016; last updated Mar. 6, 2018). "Safety and Tolerability of GemRIS 225 mg in Subjects With Muscle-Invasive Bladder Cancer," located at https://clinicaltrials.gov/ct2/history/NCT02722538?A=1&B=10&C=merged , last visited on Feb. 21, 2019, 20 pages.

clinicaltrials.gov. NCT03404791. (Jan. 19, 2018). "Safety and Tolerability of TAR-200 in Subjects With Muscle-Invasive Bladder Cancer Who Are Unfit for Radical Cystectomy," located at https://www.clinicaltrials.gov/ct2/history/NCT03404791?V_1=View , last visited on Feb. 21, 2019, 15 pages.

Cockerill, P.A. et al. (Mar. 2016; e-pub May 2, 2015.). "Intravesical Gemcitabine in Combination with Mitomycin C as Salvage Treatment in Recurrent Non-Muscle-Invasive Bladder Cancer," BJU Int. 117(3):456-462.

Cronauer, M.V. et al. (1996). "Inhibitory Effects of the Nucleotide Analogue Gemcitabine on Prostatic Carcinoma Cells," The Prostate 18:172-181.

Dalbagni, G. et al. (Jun. 20, 2006). "Phase II Trial of Intravesical Gemcitabine in Bacille Calmette-Guérin-Refractory Transitional Cell Carcinoma of the Bladder," Journal of Clinical Oncology 24(18):2729-2734.

Dall'Era, M.A. et al. (Jul. 2012). "Contemporary Management of Muscle-Invasive Bladder Cancer," Expert Rev. Anticancer Ther. 12(7):941-950, 18 pages.

Daneshmand, S. et al. (2017; e-pub. May 30, 2017). "Effect of GemRIS (Gemcitabine-Releasing Intravesical System, TAR-200) on Antitumor Activity in Muscle-Invasive Bladder Cancer (MIBC)," Journal of Clinical Oncology 35(15):suppl. e16000, located at, http://ascopubs.org/doi/abs/10.1200/JCO.2017.35.15_suppl.e16000, last visited on Feb. 21, 2019, 2 pages.

Delto, J.C. (2013). "Preclinical Analyses of Intravesical Chemotherapy For Prevention of Bladder Cancer Progression," Oncotarget 4(2):269-276.

Herr, H.W. et al. (Feb. 2007). "Defining Optimal Therapy for Muscle Invasive Bladder Cancer," The Journal of Urology 177:437-443.

International Preliminary Report on Patentability, issued Sep. 6, 2016, for PCT Application No. PCT/US2015/019262, filed Mar. 6, 2015, 11 pages.

Kamel, M.H. et al. (Dec. 2011). "Definition of BCG Failure in Non-Muscle Invasive Bladder Cancer in Major Urological Guidelines," Urotoday Int. J. 4(6):art 82, 4 pages.

Krasnyuk, I.I. et al. (2006). "Pharmaceutical Technology: Technology of Dosage Forms," Publishing Center Academy, p. 6, 4 pages. English Abstract Translation.

Kroemer, G. et al. (2013, e-pub. Nov. 12, 2012). "Immunogenic Cell Death in Cancer Therapy," Annu. Rev. Immunol. 31:51-72.

Kumaran, D. et al. (2016, e-pub. Jul. 2, 2016). "Carcinoma of Gall Bladder With Distant Metastasis to Breast Parenchyma. Report of a Case and Review of Literature," J. Egypt Natl. Canc. Inst. 28(4):263-266.

Leach, D.R. et al. (Mar. 22, 1996). "Enhancement of Antitumor Immunity by CTLA-4 Blockade," Science 271(5256):1734-1736.

Li, J. et al. (Oct. 2014). Effect of Internal Iliac Artery Chemotherapy after Transurethral Resection of Bladder Tumor For Muscle Invasive Bladder Cancer, Chin J Cancer Res. 26(5):558-563.

Lorenzo, G.D. et al. (Apr. 15, 2010, e-pub. Feb. 16, 2010). "Gemcitabine Versus Bacille Calmette-Guerin After Initial Bacille Calmette-Gue'rin Failure in Non-Muscle-Invasive Bladder Cancer,". Cancer 116:1893-1900.

Ma, J. et al. (Jul. 2016). "Overview of Gemcitabine to Prevent Bladder Cancer Recurrence," J. Mod. Urol. 21(7):562-566, with English Translation.

Matulewicz, R.S. et la. (2020). "Non-Muscle-Invasive Bladder Cancer: Overview and Contemporary Treatment Landscape of Neoadjuvant Chemoablative Therapies," Reviews in Urology 22(2):43-51.

Mertens, L.S. et al. (Oct. 2012). "Carboplatin Based Induction Chemotherapy for Nonorgan Confined Bladder Cancer—A Reasonable Alternative for Cisplatin Unfit Patients?" Journal of Urology 188:1108-1114.

Oh, K.S. et al. (Nov. 2, 2009). "Combined-Modality Therapy With Gemcitabine and Radiation Therapy as a Bladder Preservation Strategy: Long-Term Results of a Phase I Trial," International Journal of Radiation: Oncology Biology Physics 74(2):511-517.

Oliveira, M.B. et al. (Apr. 12, 2017). "A Review of Recent Developments on Micro/Nanostructured Pharmaceutical Systems for Intravesical Therapy of the Bladder Cancer," Pharmaceutical Development and Technology 23(1):1-12.

O'Donnell, P.H. et al. (Mar. 1, 2015). "Prembrolizumab (Pemfro; MK-3475) for Advanced Urothelial Cancer: Results of a Phase IB Study," Journal of Clinical Oncology 33(7):296, 4 pages.

Pardoll, D.M. (Apr. 2012, e-pub. Mar. 22, 2012). "The Blockade Of Immune Checkpoints In Cancer Immunotherapy," Nat. Rev. Cancer 12(4): 252-264.

Prasanna, T. et al. (Nov. 2, 2017). "Intravesical Gemcitabine Versus Intravesical Bacillus Calmette-Guerin for the Treatment of Non-Muscle Invasive Bladder Cancer: An Evaluation of Efficacy and Toxicity," Frontiers in Oncology 7(260):1-5.

Seront, E. et al. (Jan. 1, 2015). "Molecular Biology and Targeted Therapies for Urothelial Carcinoma," Cancer Treatment Reviews 41:341-353.

Shariat, S.F. et al. (May 2010). "Update on Intravesical Agents For Non-Muscle-Invasive Bladder Cancer," Immunotherapy 2(3):381-392, 19 pages.

Stadler, W.M. et al. (Nov. 1997). "Phase II Study of Single-Agent Gemcitabine in Previously Untreated Patients With Metastatic Urothelial Cancer," J. of Clinical Oncology 15(11):3394-3398.

Sternberg, I.A. et al. (Nov. 2013). "Intravesical Gemcitabine for High Risk, Nonmuscle Invasive Balder Cancer After Bacillus Calmette-Guerin Treatment Failure," Journal of Urology 190(5):1686-1691.

Sultan, G. et al. (2016). "Neoadjuvant Chemotherapy for Transitional Cell Carcinoma of the Bladder: A Single Centre Experience," Journal of Life Sciences 10:85-90.

Tsai, Y.-H. et al. (Nov. 2010). "Microemulsions For Intravesical Delivery of Gemcitabine," Chem. Pharm. Bull. 58(11):1461-1465.

Voena, C. et al. (Feb. 2016). "Advances in Cancer Immunology and Cancer Immunotherapy," Discovery Medicine 21(114):125-133.

Vogelzang, N.J. et al. (1999). "Gemcitabine and Other New Chemotherapeutic Agents For The Treatment of Metastatic Bladder Cancer," Urology 53:243-250.

(56)　　　　　References Cited

OTHER PUBLICATIONS

Waddell, J.A. et al. (Dec. 2004). "Intravesical Gemcitabine for Superficial Bladder Carcinoma," Hospital Pharmacy 39(12):1153-1154.

Wolchok, J.D. et al. (2008). "The Mechanism of Anti-CTLA-4 Activity and the Negative Regulation of T-Cell Activation," The Oncologist 13(Suppl 4):2-9.

Yuh, B.E. et al. (May 2013). "Pooled Analysis of Clinical Outcomes with Neoadjuvant Cisplatin and Gemcitabine Chemotherapy for Muscle Invasive Bladder Cancer," Journal of Urology 189:1682-1686.

Food and Drug Administration: Center For Drug Evaluation And Research (CDER). (Jul. 2005). "Guidance for Industry: Estimating the Maximum Safe Starting Dose in Initial Clinical Trials for Therapeutics in Adult Healthy Volunteers," Pharmacology and Toxicology, 30 pages.

U.S. Appl. No. 18/181,467, filed Mar. 9, 2023 by Giesing et al. (Copy not submitted herewith pursuant to the waiver of 37 C.F.R. § 1.98(a)(2)(iii) issued by the Office on Sep. 21, 2004.).

Addeo, R. et al. (Feb. 1, 2010). "Randomized Phase III Trial on Gemcitabine Versus Mitomycin in Recurrent Superficial Bladder Cancer: Evaluation of Efficacy and Tolerance," J Clin Oncol. 28(4):543-548.

Balar, A. V. et al. (Feb. 26, 2019). "Keynote 057: Phase II Trial of Pembrolizumab (Pembro) for Patients (pts) with High-risk (HR) Nonmuscle Invasive Bladder Cancer (NMIBC) Unresponsive to Bacillus Calmette-Guerin (BCG)," Journal of Clinical Oncology 37(7):Supplement 350, 3 pages. Abstract.

Balar, A. V. et al. (Jul. 2021, e-pub. May 26, 2021). "Pembrolizumab Monotherapy for the Treatment of High-risk Non-muscle-invasive Bladder Cancer Unresponsive to BCG (KEYNOTE-057): An Open-label, Single-arm, Multicentre, Phase 2 Study," The Lancet. Oncology 22(7):919-930.

Bamias, A. et al. (Jun. 2016). "Outcome of Patients with Nonmetastatic Muscle-Invasive Bladder Cancer Not Undergoing Cystectomy after Treatment with Noncisplatin-Based Chemotherapy and/or Radiotherapy: A Retrospective Analysis," Cancer Med. 5(6):1098-1107.

Dinney, C. P. N. et al. (2013). "Intravesical Valrubicin in Patients with Bladder Carcinoma in Situ and Contraindication to or Failure after Bacillus Calmette-Guérin," Urol Oncol. 31(8):1635-1642.

Eriksson, E. (2016, e-pub. Sep. 29, 2016). "Gemcitabine Reduces MDSCs, Tregs and TGFBeta-1 While Restoring the Teff/Treg Ratio in Patients with Pancreatic Cancer," Journal of Translational Medicine 14(282):12 pages.

Fujii, Y. (Mar. 2018, e-pub. Dec. 16, 2017). "Prediction Models for Progression of Non-muscle-invasive Bladder Cancer: A Review," Int J Urol. 25(3):212-218.

Lee, H. et al. (Jan. 20, 2011). "An Intravesical Device for The Sustained Delivery of Lidocaine to the Bladder," J Control Release 149(2):133-139.

Mirza, A. et al. (2016, e-pub. Apr. 27, 2016). "Bladder Preservation for Muscle Invasive Bladder Cancer," BI Cancer 2(2):151-163.

Necchi, A. et al. (May 3, 2024). "P2-01 TAR-200 in Patients with Bacillus Calmette-Guérin-Unresponsive High-risk Non-muscle-invasive Bladder Cancer: Results from Sunrise-1 Study," Journal of Urology 211(5S2):E1.

Sylvester, R. J. et al. (2016). "Systematic Review and Individual Patient Data Meta-Analysis of Randomized Trials Comparing a Single Immediate Instillation of Chemotherapy After Transurethral Resection with Transurethral Resection Alone in Patients with Stage pTa-pT1 Urothelial Carcinoma of the Bladder: Which Patients Benefit from the Instillation?" European Urology 69(2):231-244.

Tan, W. S. et al. (2018, e-pub. Sep. 25, 2018). "Intravesical Device-assisted Therapies for Non-muscle-invasive Bladder Cancer," Nat Rev Urol 15(11):667-685, 18 pages.

Woldu, S. et al. (Mar. 2017). "Guideline of Guidelines—Non-Muscle Invasive Bladder Cancer," BJU Int. 119(3):371-380.

Zhao, P. et al. (Jan. 2017, e-pub. Nov. 17, 2016). "Gemcitabine Treatment Enhanced the Anti-Tumor Effect of Cytokine Induced Killer Cells by Depletion of CD4+CD25bri Regulatory T Cells," Immunology Letters 181:36-44.

* cited by examiner

402

400

400

400

400

402

650

600

660

602

METHODS FOR TREATMENT OF BLADDER CANCER WITH GEMCITABINE

CROSS-REFERENCE TO RELATED APPLICATIONS

This application is a continuation of U.S. patent application Ser. No. 17/561,540, filed Dec. 23, 2021, which is a continuation of U.S. patent application Ser. No. 14/641,009, filed Mar. 6, 2015, which claims the benefit of U.S. Provisional Patent Application No. 61/949,215, filed Mar. 6, 2014. These applications are incorporated herein by reference.

FIELD OF INVENTION

The present invention relates generation to the treatment of cancer, and more particularly relates to compositions, devices, and methods for the treatment of urinary bladder cancers.

BACKGROUND

Bladder cancer is a significant medical problem, and currently available treatment options are unsatisfactory for a number of reasons.

In general, bladder cancers are classified as muscle invasive bladder cancer (MIBC) or non-muscle invasive bladder cancer (NMIBC). The pathological classification and staging of bladder cancer is as follows: pTa (urothelial involvement); pTis (high risk urothelial confined); pT1 (lamina propria invasion); pT2 (muscularis invasion); pT3 (perivesical fat invasion); and pT4 (pelvic organ extension). Bladder cancers can also be classified by grade as Grade 1/3 (well differentiated); Grade 2/3 (moderately differentiated); Grade 3/3 (poorly differentiated). In addition, bladder cancers can be classified by stage as Stages 0-IV. Most bladder cancers are transitional cell carcinomas of epithelial origin and classified as non-muscle invasive cancer (NMIBC) confined to the inner lining of the bladder. At initial presentation, most bladder cancers are superficial NMIBCs and include stages pTa, pTis and pT1 disease. MIBC include stages pT2, pT3 and pT4.

The typical clinical protocol of early stage bladder cancer is cystoscopy visualization followed by surgical removal of the tumor(s), known as transurethral resection (TUR). However, there is a high rate of recurrence after surgery and the cancer may progress to muscle-invasive disease. Therefore, surgery is often combined with adjuvant intravesicular installation (direct administration of the chemotherapeutic agent into the bladder through a catheter) of chemotherapeutic or immunotherapeutic agents to help prevent or delay the incidence and severity of recurrence. Bacile Calmette-Guerin (BCG) is such an immunotherapeutic and is typically instilled into the bladder following surgery. However, many patients do not respond to BCG, and BCG treatment can also induce a range of adverse effects leading to discontinuation of treatment. Chemotherapeutic agents are usually reserved for patients who have failed BCG therapy. Chemotherapy is typically applied intravesically to concentrate the chemotherapeutic agent at the tumor sites and eliminate any residual tumor after resection while avoiding systemic exposure of the drug.

One such chemotherapeutic agent used in clinical trials for treating bladder cancer is gemcitabine. Gemcitabine (2',2'-difluorodeoxycytidine) is a pyrimidine analogue with activity against metastatic bladder cancer. Gemcitabine has also been used in clinical trials to treat superficial bladder cancers and NMIBC by instillation in the bladder with various weekly schedules. Gemcitabine is typically instilled over 1 to 2 hours once or twice a week for several weeks at doses typically ranging from 500 to 2000 mg in up to 100 ml of saline.

It is known that such formulations are voided from the bladder before full efficacy is achieved. The short dwell times of 1 to 2 hours limit therapeutic benefit. In addition, high concentrations (40 mg/ml) and high doses (up to 2 grams per instillation) are used in an attempt to achieve therapeutic tissue levels in order to try to overcome the dwell time limitations. However, intravesical administration of high doses of gemcitabine can lead to significant systemic absorption and cause gastrointestinal, bladder and bone marrow toxicity further limiting the clinical utility in addition to local tolerability issues.

The literature also reports that intravenous systemic administration of gemcitabine by bolus injection, e.g., over 1 to 2 minutes, is better tolerated by patients than slow intravenous infusion, e.g., over 90 minutes. This suggests that prolonged exposure to gemcitabine increases toxicity and should be avoided.

Accordingly, there remains a need for improved drug delivery methods and systems for treating bladder cancer. For example, there remains a need to administer therapeutic levels of gemcitabine to patient over sustained periods while avoiding or mitigating toxicity and tolerability issues that have been observed to limit the clinical utility of gemcitabine.

BRIEF SUMMARY

In one aspect, a medicament is provided which comprises gemcitabine for use in the treatment of bladder cancer by locally administering the gemcitabine into the bladder of a patient to achieve a sustained concentration of the gemcitabine in the urine in the bladder sufficient to produce a therapeutic concentration of the gemcitabine in the bladder tissues, wherein the local administration into the patient's bladder is at a mean average amount of from 1 mg/day to about 300 mg/day of the gemcitabine free base equivalent (FBE). In embodiments, the local administer into the patient's bladder is at a mean average amount of from 1 mg/day to 200 mg/day of the gemcitabine (FBE), from 5 mg/day to 100 mg/day of the gemcitabine (FBE), from 10 mg/day to 50 mg/day of the gemcitabine (FBE), or from 15 mg/day to 25 mg/day of the gemcitabine (FBE). In one case, the locally administering into the patient's bladder is at a mean average amount of about 20 mg/day of the gemcitabine (FBE). The local administer into the patient's bladder may be continuous or intermittent. In embodiments, the continuous or intermittent administration is over a period from 1 day to 30 days, from 1 day to 14 days, or from 1 day to 7 days.

In a preferred embodiment, the gemcitabine is delivered into the bladder from an intravesical drug delivery device which continuously releases the gemcitabine into the urine in the bladder over a sustained period. In another embodiment, the gemcitabine is delivered into the bladder from a coating substance applied to the bladder, which coating substance (e.g., a mucoadhesive formulation) releases the gemcitabine into the urine in the bladder over a sustained period. In still another embodiment, a liquid form of the gemcitabine is pumped into the bladder over a sustained period through a urethral or suprapubic catheter which is deployed into the bladder.

In another aspect, a drug delivery device is provided for administering gemcitabine to a patient in need of treatment of bladder cancer by intravesically administering gemcitabine into the bladder of the patient to achieve a sustained concentration of the gemcitabine in urine in the bladder sufficient to produce a therapeutically effective concentration of the gemcitabine in the tissues of the bladder. In a particular embodiment, the drug delivery device includes a housing configured for intravesical insertion, and a dosage form comprising gemcitabine, wherein the housing holds the dosage form and is configured to release the gemcitabine into the bladder in an amount therapeutically effective for the treatment of the bladder, wherein the device is configured to release gemcitabine into the bladder at a mean average amount of from 1 mg/day to about 300 mg/day of the gemcitabine. In a preferred embodiment, the housing releases the gemcitabine without a predefined release aperture. In a particular version of this preferred embodiment, the housing releases the gemcitabine by diffusion through a drug permeable polymeric wall. The housing which contains and controllably releases the gemcitabine may be elastically deformable between a retention shape configured to retain the device in a patient's bladder and a deployment shape for passage of the device through the patient's urethra.

In still another aspect, methods of treating bladder cancer are provide by locally administering the gemcitabine into the bladder of a patient to achieve a sustained concentration of the gemcitabine in the urine in the bladder sufficient to produce a therapeutic concentration of the gemcitabine in the bladder tissues. In embodiments, the local administration into the patient's bladder is at a mean average amount of from 1 mg/day to about 300 mg/day of the gemcitabine (FBE). In one embodiment, the method further includes administering at least a second therapeutic agent to the patient. The second therapeutic agent may be administered intravesically. In another embodiment, the method further includes administering urea or another solubility altering agent into the bladder in an amount effective to enhance or otherwise alter solubilization of the gemcitabine. In embodiments, the second therapeutic agent and/or the solubility altering agent is released from an intravesical device which releases the gemcitabine.

BRIEF DESCRIPTION OF THE DRAWINGS

FIG. 10A is a plan view of the device. FIG. 10B is a cross-sectional view of one of the four drug reservoir modules of the device shown in FIG. 10A, showing the drug tablets and permeation disks of each module. FIG. 10C is a perspective view of a portion of the housing/body portion of the device shown in FIG. 10A before assembly with the other components of the device.

DETAILED DESCRIPTION

Figure 1A:
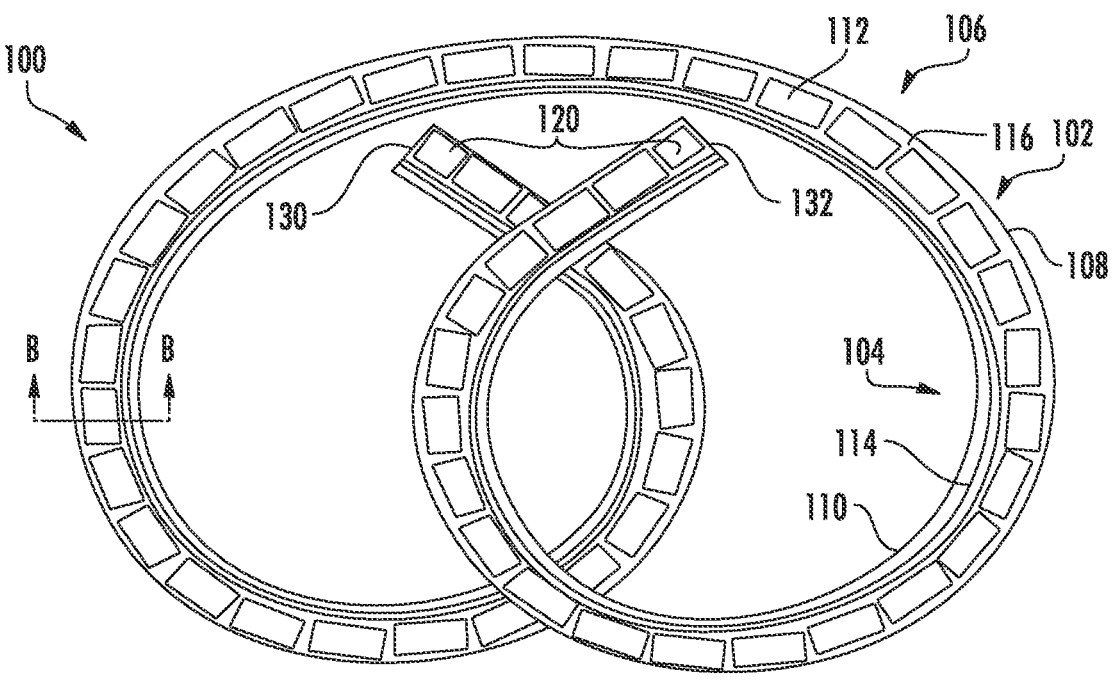
FIGS. 1A-1B illustrate one embodiment of an intravesical drug delivery device that may be used for administering gemcitabine as described herein.

It has been discovered that continuous delivery of gemcitabine by intravesical administration yielded unexpected drug distribution across the bladder wall and achieved drug levels at or above the projected therapeutic threshold in all layers of the bladder—without significant plasma/systemic exposure. Accordingly, the compositions, systems, and methods described herein can be used to achieve therapeutically effective amounts of gemcitabine in the tissues of the bladder where needed, while also being well tolerated by the normal bladder tissue and minimizing systemic exposure.

As used herein, the term "gemcitabine" includes the compound gemcitabine as well as its pharmaceutically acceptable salts, esters, amides, solvates and prodrugs. In particular, the hydrochloride salt of gemcitabine is included. The gemcitabine may be formulated with one or more suitable pharmaceutically acceptable excipients.

In certain embodiments, a controlled amount of gemcitabine is dissolved in urine in the patient's bladder in a concentration and over a time sufficient to produce and maintain therapeutic concentrations of the drug in tissues of the bladder. However, because the bladder limits the absorption of urine components into the general circulation, systemic exposure to the drug is advantageously minimized.

A variety of methods can be used to achieve the required urine concentrations of the gemcitabine. In one embodiment, the drug can be provided by direct instillation of a simple solution into the bladder. For example, a solution of the drug may be pumped into the bladder through a urethral or suprapubic catheter in a continuous or pulsatile manner over the treatment period. In another embodiment, the drug is released from a device or composition deployed in the bladder, wherein the device or composition releases the drug (continuously or intermittently) at a rate effective to produce the desired concentration of drug in the urine over a specified treatment period. For example, the drug may be released from an intravesically-inserted device into the bladder and then the drug diffuses into the bladder. At the end of the treatment period, the device may be retrieved from the bladder, or it may be eliminated by being resorbed, dissolved, excreted, or a combination thereof.

In a preferred embodiment, the gemcitabine is administered to the bladder from an intravesical device. Examples of intravesical drug delivery devices, which can be tailored to achieve the dosage regimens described herein, and methods of deploying those devices into the bladder are described in the following U.S. Patent Application Publications: US 2012/0203203 (Lee et al.); US 2012/0089122 (Lee et al.); US 2012/0089121 (Lee et al.); US 2011/0218488 (Boyko et al.); US 2011/0202036 (Boyko et al.); US 2011/0152839 (Cima et al.); US 2011/0060309 (Lee et al.); US 2010/0331770 (Lee et al.); US 2010/0330149 (Daniel et al.); US 2010/0003297 (Tobias et al.); US 2009/0149833 (Cima et al.); US 2007/0202151 (Lee et al.); WO 2014/144066 (Lee et al.); U.S. 2014/0276636 (Lee et al.); and WO 2015/026813 (Lee et al.).

In embodiments in which the gemcitabine is delivered from an intravesical drug delivery device, the drug may be housed in the device in various forms, which may depend on the particular mechanism by which the device controllably releases the drug into fluid (e.g., urine) in the bladder. In some embodiments, the drug is provided in a solid, semi-solid, or other non-liquid form, which advantageously may facilitate stable storage of the drug before the device is used and advantageously may enable the drug payload of the device to be stored in smaller volume than would be possible if the drug were housed in the form of a liquid solution. In an embodiment, the non-liquid form is selected from tablets, granules, semisolids (e.g., an ointment, cream, paste, or gel), capsules, and combinations thereof. In one embodiment, the drug is in the form of a plurality of tablets, such as mini-tablets described in U.S. Pat. No. 8,343,516. In other embodiments, the drug may be housed in a liquid form, such as in a solution with one or more pharmaceutically acceptable excipients.

An embodiment of a drug delivery device 100 is illustrated in FIG. 1A. The device 100 includes a device body having a drug reservoir portion 102 and a retention frame portion 104. In FIG. 1, the device 100 is shown in a relatively expanded shape suited for retention in the body. Following deployment into the body, the device 100 may assume the relatively expanded shape to retain the drug delivery device in the body cavity or lumen.

For the purposes of this disclosure, terms such as "relatively expanded shape," "relatively higher-profile shape," or "retention shape" generally denote any shape suited for retaining the device in the intended implantation location, including but not limited to the pretzel shape shown in FIG. 1 that is suited for retaining the device in the bladder. Similarly, terms such as "relatively lower-profile shape" or "deployment shape" generally denote any shape suited for deploying the drug delivery device into the body, including a linear or elongated shape that is suited for deploying the device through the working channel of catheter, cystoscope, or other deployment instrument positioned in the urethra. In embodiments, the drug delivery device may naturally assume the relatively expanded shape and may be deformed, either manually or with the aid of an external apparatus, into the relatively lower-profile shape for insertion into the body. Once deployed the device may spontaneously or naturally return to the initial, relatively expanded shape for retention in the body.

In the illustrated embodiment, the drug reservoir and retention frame portions 102, 104 of the drug delivery device 100 are longitudinally aligned and are coupled to each other along their length, although other configurations are possible. The drug delivery device 100 includes an elastic or flexible device body 106 that defines a drug reservoir lumen 108 (i.e., the drug housing) and a retention frame lumen 110. The drug reservoir lumen 108 is designed to house a drug formulation that comprises the drug. In the illustrated embodiment, the drug formulation comprising gemcitabine is in the form of a number of solid drug units 112, which may be tablets. The retention frame lumen 110 is designed to house a retention frame 114 to form the retention frame portion 104. The illustrated lumens 108, 110 are discrete from each other, although other configurations are possible.

Figure 1B:
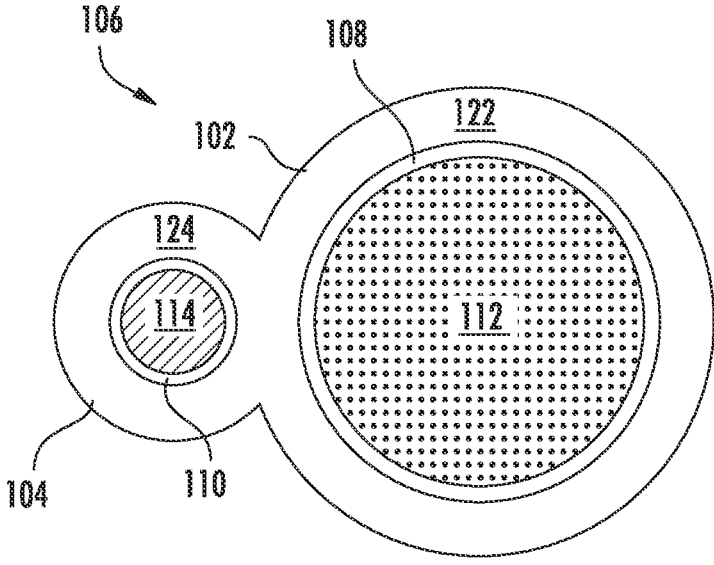

As shown in the cross-sectional view of FIG. 1B, the device body 106 includes a tube or wall 122 that defines the drug reservoir lumen 108 and a tube or wall 124 that defines the retention frame lumen 110. The tubes 122, 124 and lumens 108, 110 can be substantially cylindrical, with the drug reservoir lumen 108 having a relatively larger diameter than the retention frame lumen 110, although other configurations can be selected based on, for example, the amount of drug to be delivered, the diameter of the retention frame, and deployment considerations such as the inner diameter of the deployment instrument. The wall 124 that defines the retention frame lumen 110 may extend along the entire length of the wall 122 that defines the drug reservoir lumen 108, so that the retention frame lumen 110 has the same length as the drug reservoir lumen 108 as shown, although one wall may be shorter than the other wall in other embodiments. The two walls 122, 124 are attached along the entire length of the device in the illustrated embodiment, although intermittent attachment can be employed.

As shown in FIG. 1A, the drug reservoir lumen 108 is loaded with a number of drug units 112 (comprising gemcitabine) in a serial arrangement. Essentially any number of drug units may be used, for example, depending upon the sizes of the reservoir and the drug units. The drug reservoir lumen 108 includes a first end opening 130 and an opposed second end opening 132. Once the drug units 112 are loaded, restraining plugs 120 are disposed in the openings 130 and 132. The restraining plugs 120, in this embodiment, are cylindrical plugs secured into the openings 130, 132. In other embodiments, the openings 130 and 132 are closed off with other structures or materials, which may, depending on the particular embodiments, include an aperture or a water- or drug-permeable wall to facilitate ingress or egress of water or drug during use.

In other embodiments, the drug reservoir lumen may be loaded with gemcitabine forms other than as solid drug units. For example, gemcitabine, may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

In one embodiment, the gemcitabine is formulated with one or more excipients that include a viscosity enhancing agent to control release of solubilized gemcitabine from a release aperture in the device housing. In another embodiment, the device reservoir includes both gemcitabine and a viscosity enhancing agent, but they are not co-formulated and instead are provide in discrete regions within the reservoir, e.g., as separate tablets. Suitable viscosity enhancing agents, including but not limited to polyethylene oxide (PEO), are known in the pharmaceutical arts. In some variations of the embodiment, the viscosity enhancing agent may be provided, e.g., formulated, with urea or another osmotic agent.

In one embodiment, the gemcitabine is administered to the patient with a solubility enhancing agent. In an embodiment, the solubility enhancing agent is urea. In one embodiment, the urea is provided in a tablet or other solid form and loaded with the gemcitabine in the drug reservoir of an intravesical drug delivery device. The urea may also function, depending on the device, as an osmotic agent to facilitate generation of an osmotic pressure in a drug reservoir. In a particular embodiment, the gemcitabine and the osmotic agent are configured as separate tablets (or other solid forms) positioned within different regions of the drug reservoir as described in PCT WO 2015/026813 (Lee et al.) which is incorporated by reference herein.

The retention frame lumen 110 is loaded with the retention frame 114, which may be an elastic wire, e.g., a superelastic alloy such as nitinol. The retention frame 110 may be configured to return spontaneously to a retention shape, such as the illustrated example "pretzel" shape or another coiled shape, such as those disclosed in the applications previously incorporated. In particular, the retention frame 114 may retain the device 100 in the body, such as in the bladder. For example, the retention frame 114 may have an elastic limit and modulus that allows the device 100 to be introduced into the body in a relatively lower-profile shape, permits the device 100 to return to the relatively expanded shape once inside the body, and impedes the device from assuming the relatively lower-profile shape within the body in response to expected forces, such as the hydrodynamic forces associated with contraction of the detrusor muscle and urination. Thus, the device 100 may be retained in the body once implanted, limiting or prevent accidental expulsion.

The material used to form the device body 106, at least in part, may be elastic or flexible to permit moving the device 100 between deployment and retention shapes. When the device is in the retention shape, the retention frame portion 104 may tend to lie inside the drug reservoir portion 102 as shown, although the retention frame portion 104 can be positioned inside, outside, above, or below the drug reservoir portion 102 in other cases.

The material used to form the device body 106 may be water permeable so that solubilizing fluid (e.g., urine) can enter the drug reservoir portion 102 to solubilize the drug units 112 once the device is implanted. For example, silicone or another biocompatible elastomeric material may be used. In other embodiments, the device body may be formed, at least in part, of a water-impermeable material.

Figure 2A:
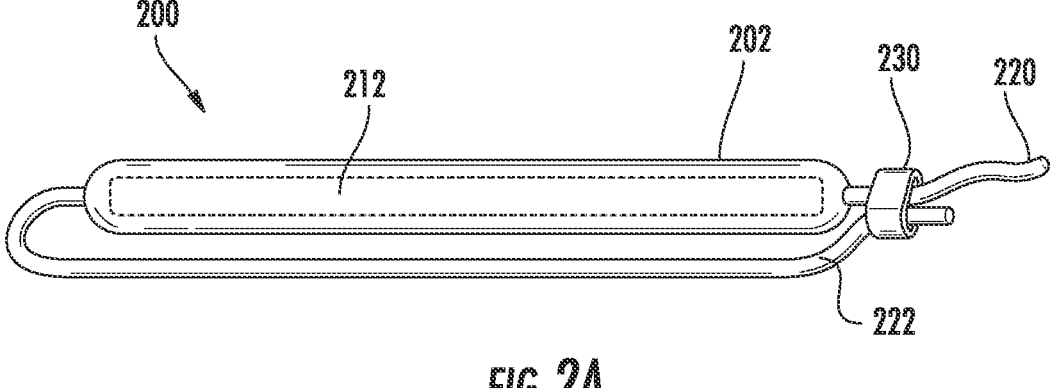
FIGS. 2A-2B illustrate another embodiment of an intravesical drug delivery device that may be used for administering gemcitabine as described herein.
Figure 2B:
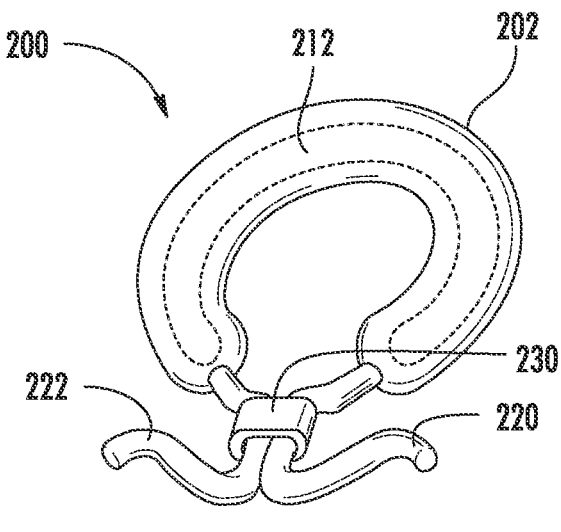

FIG. 2A illustrates another embodiment of an intravesical drug delivery device 200, which includes a drug reservoir 202 loaded with drug 212 and a retention structure that includes two filaments 220, 222 associated with a fastener 230. As shown, the drug reservoir 202 is an elongated tube that can be deformed between a relatively linear deployment shape, such as the shape shown in FIG. 2A, and a relatively circular retention shape, such as the shape shown in FIG. 2B. The drug 212 may be loaded in the tube in a flexible form, so that the drug reservoir 202 can be moved between the two shapes. For example, the drug 212 may be a number of solid drug tablets, a liquid, or a gel. The filaments 220, 222 may be attached to opposite ends of the drug reservoir 202 and joined by the fastener 230. The fastener 230 can be adjusted to adjust the position of one filament 220 with reference to the other 222, thereby adjusting the position of one end of the drug reservoir 202 with reference to the other end. The device 200 can assume the retention shape by adjusting the filaments 220, 222 to draw the ends of the drug reservoir 202 closer together, and thereafter the device 200 can be retained in the retention shape by preventing adjustment of the filaments 220, 222 with the fastener 230. In such an embodiment, the device 200 is manually adjusted into the retention shape by manually adjusting the filaments 220, 222 after the device 200 is inserted into the bladder.

In the illustrated embodiment, the fastener 230 is a cinch nut that permits shortening the portion of the filaments 220, 222 between the drug reservoir ends and the cinch nut, but prevents lengthening of these portions of the filaments 220, 222. Thus, the ends of the drug reservoir 202 can be drawn closer together by pulling one or both of the filaments 220, 222 through the cinch nut, causing the device 200 to assume the retention shape. Once the filaments 220, 222 have been so adjusted, the cinch nut prevents lengthening of the filaments 220, 222, retaining the device in the retention shape. Thus, manually adjusting the device 200 into the retention shape once implanted merely requires pulling one or both of the filaments 220, 222, although other fasteners 230 that require separate manipulation can be employed. Other fasteners may also be used.

Figures 3A, 3B, 3C:
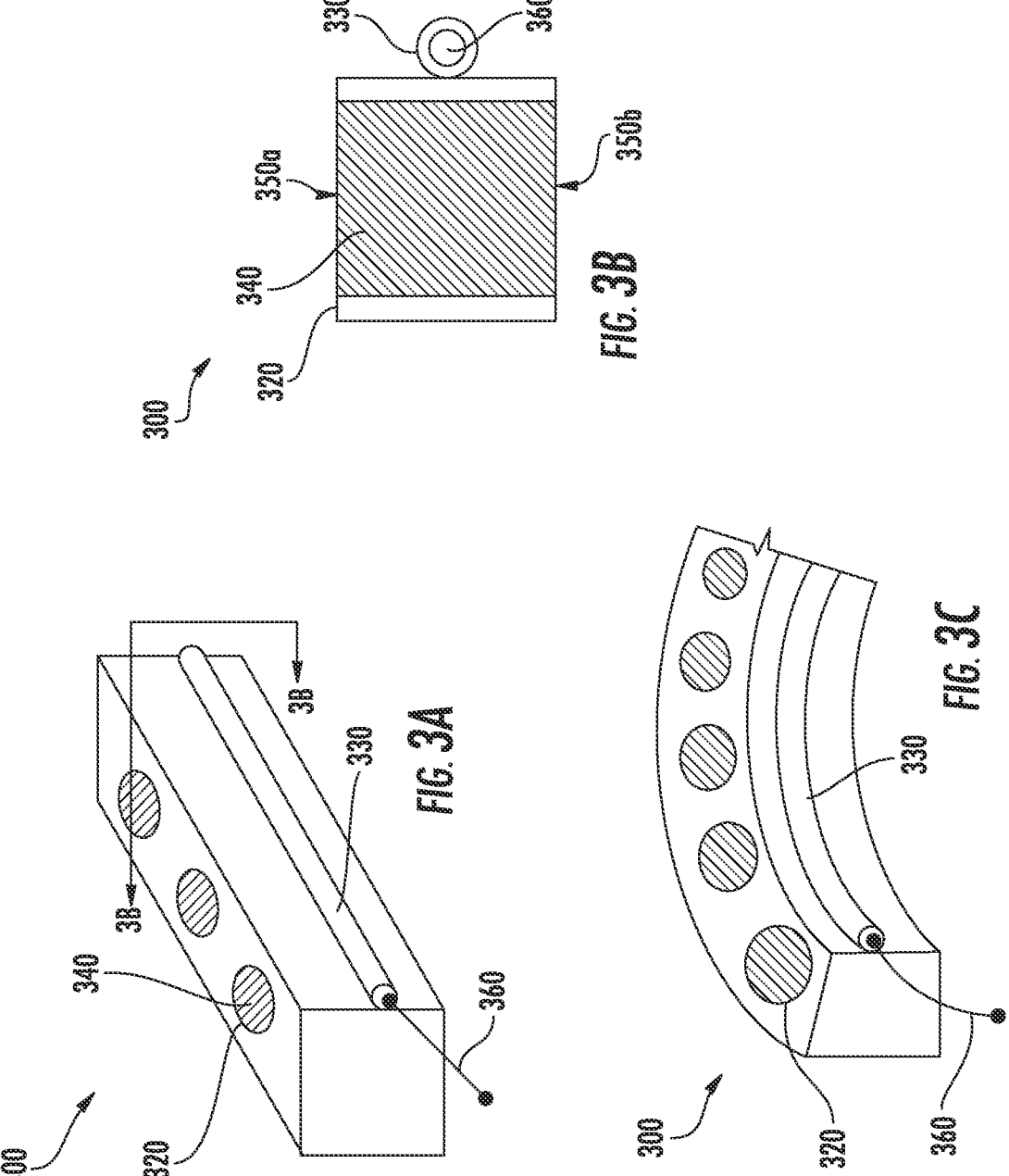
FIGS. 3A-3C illustrate still another embodiment of an intravesical drug delivery device that may be used for administering gemcitabine as described herein.

Another embodiment of an intravesical drug delivery device is illustrated in FIGS. 3A-3C. In this embodiment, the device includes a housing 300 having a single, continuous structure with multiple, discrete drug reservoir lumens 320 and optionally having at least one retention frame lumen 330 in which a retention frame 360 is disposed. Each drug reservoir lumen 320 has two defined openings, as shown a cross-sectional view in FIG. 3B, and is dimensioned to hold at least one solid drug unit 340. For example, solid drug unit 340 may be a drug tablet or capsule. In another embodiment, not shown, each drug reservoir lumen has a single defined opening. The housing may be formed of a flexible polymer, such as silicone. FIG. 3B is a cross-sectional view of the plane that bisects one of the drug reservoir lumens 320 of the housing shown in FIG. 3A along line 3B-3B. As shown in FIG. 3B, the monolithic housing 300 has two defined openings (350a, 350b) in its drug reservoir lumen 320 that expose both ends of the solid drug unit 340. The retention frame lumen 330, in this embodiment, is aligned parallel to the longitudinal axis of the housing and perpendicular to the drug reservoir lumen 320. FIG. 3C is a perspective view of a portion of the embodiment of the device 300 shown in FIG. 3A when the device is in its retention shape, which is taken when the retention frame 360 is disposed in the retention frame lumen 330. The drug reservoir lumens 320 and the retention frame 360 in the housing of this embodiment are oriented so that the drug reservoir lumens 320 are outside the arc of the retention frame 360. Alternatively, the housing in FIG. 3C can be rotated 180 degrees about the retention frame 360 to yield a configuration in which the drug reservoir lumens 320 are arranged within the retention frame's 360 arc. With this embodiment, the devices provide sufficient direct contact between solid drug units and with urine surrounding the device when deployed and retained in the bladder. In embodiments, release of the drug from the device is controlled by erosion of an exposed portion of the surface of a solid drug unit, such that the rate of drug release from the drug delivery device may be directly proportional to and limited by the total exposed surface area of the solid drug units.

The release of gemcitabine from the intravesical devices described herein may be driven and controlled by different mechanisms of action. In various embodiments, the drug may be released from the intravesical drug delivery device by diffusion to through a wall of the drug housing, by diffusion to through one or more defined apertures in a wall of the drug housing, by osmotic pressure through an aperture in the drug housing, by osmotic pressure through one or more transiently formed microchannels, by erosion of a drug formulation in contact with urine in the bladder, or by a combination thereof. In a preferred embodiment, drug release is controlled by drug diffusion through a drug-permeable polymer or matrix component defining part of the device housing. In one embodiment, the device includes a drug-permeable polymer component.

In a particular embodiment, the drug delivery device includes a housing having a closed drug reservoir lumen bounded by a first wall structure and a hydrophilic second wall structure; and a drug formulation comprising gemcitabine contained in the drug reservoir lumen, wherein the first wall structure is permeable or impermeable to water and impermeable to the drug, and the second wall structure is permeable to the gemcitabine. The walls bounding and defining the drug reservoir of the device are made of a first material that serves as the first wall structure and a second material that serves as the second wall structure, such that drug release occurs essentially only through the second material. In one embodiment, the device does not include an aperture; drug release is only by diffusion through the second wall structure. As used herein, the terms "impermeable to the drug" and "impermeable to water" refer to the wall structure being substantially impermeable to the drug or to water, such that essentially no drug or water is released via the wall structure over the therapeutic release period. For use in the bladder, it is desirable that the device be compliant (i.e., easily flexed, soft feeling) during detrusor muscle contraction in order to avoid or mitigate discomfort and irritation to the patient. Thus, the durometer of the first and second materials of construction are a design consideration, and the proportion of a high durometer material may be limited in constructing a device housing of a given size while keeping it suitably compliant in the bladder. For example, Tecophilic™ thermoplastic polyurethane (Lubrizol Corp.) may have a Shore hardness greater than 70A, such as from 80A to 65D, while silicone tubing which may have a Shore hardness of from 50A to 70A. Accordingly, it can be advantageous to utilize the combination of these two different polymeric materials, rather than making the device entirely of the water-swelling hydrophilic, drug-permeable second material.

Continuing with this particular embodiment, the first wall structure may be formed of a silicone. For example, the housing may include a silicone tube, the wall of the silicone tube serving as the first wall structure. In other embodiments, the first wall structure may be formed of other water permeable materials. The drug preferably is in a solid form (e.g., a tablet or plurality of tablets) and the first wall structure is water permeable to permit in vivo solubilization of the drug while in the drug reservoir lumen. For example, the first wall structure may be formed of silicone having a Shore durometer value from about 50A to about 70A. The second wall structure may be a hydrophilic polymer, which is designed to absorb water. For example, the second wall structure may be a hydrophilic elastomeric material, which is at least partially made of hydrophilic polyurethane, hydrophilic polyesters, or hydrophilic polyamides. In a preferred embodiment, the second wall structure includes a thermoplastic polyurethane, such as Tecophilic™ thermoplastic polyurethane, HydroThane™ thermoplastic polyurethane (AdvanSource Biomaterials Corp.), Quadraphilic™ thermoplastic polyurethane (Biomerics, LLC) (ALC grades are aliphatic polycarbonate-based and ALE grades are aliphatic polyether-based hydrophilic polyurethanes), HydroMed™ (AdvanSource Biomaterials Corp.), or Dryflex® (HEXPOL TPE). Another hydrophilic polymer is polyether block amide Pebax® MV 1074 SA 01 MED (Arkema), which is a thermoplastic elastomer made of flexible and hydrophilic polyether and rigid polyamide. For example, the hydrophilic material of the second wall structure may have a Shore durometer value from about 70A to about 65D. The particular material and its thickness and wall area can be selected to control the water and drug permeation rates and thereby achieve a particular release profile of the gemcitabine.

The arrangement of the first and second wall structures can take a variety of forms. In certain embodiments, the first wall structure is a cylindrical tube and the second wall structure is an end wall disposed at least one end of the cylindrical tube, or the first wall structure and the second wall structure are adjacent one another and together form a cylindrical tube. That is, drug release is controlled by drug diffusion through a drug-permeable component defining a portion of the closed device housing. The drug-permeable wall structure may be located, dimensioned, and have material properties to provide the desired rate of controlled drug diffusion from the device. In one embodiment, as described in Example 4 below, the first wall structure is a cylindrical tube and the second wall structure is an end wall disposed at least one end of the cylindrical tube.

Figure 4A:
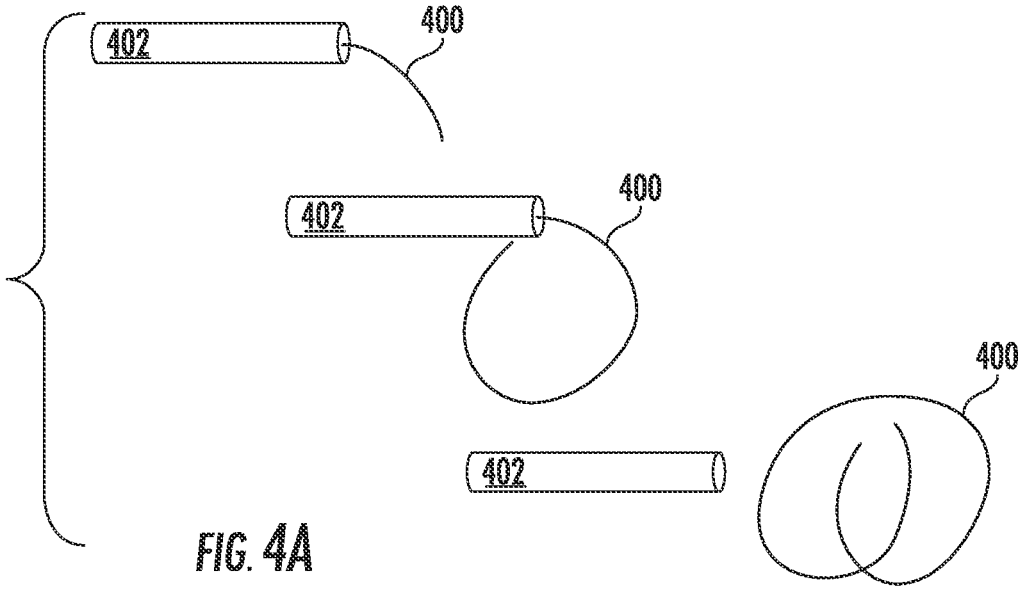
FIGS. 4A-4B illustrate a method of inserting an intravesical drug delivery device into the bladder of a patient for local administration of gemcitabine as described herein.
Figure 4B:
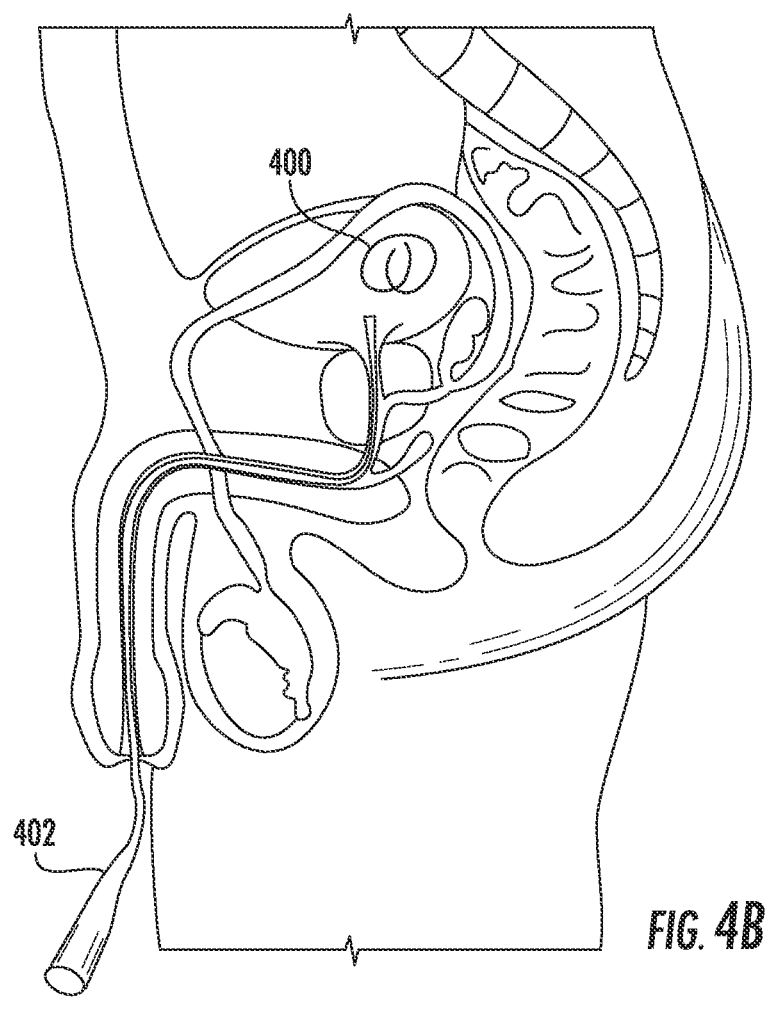

One embodiment of inserting an intravesical device 400 for subsequent controlled release of the drug into the bladder is shown in FIGS. 4A and 4B. Here, the device 400 is shown assuming a retention shape as the device exits a deployment instrument 402. The deployment instrument 402 may be any suitable device. It may be a lumenal device, such as a catheter, urethral catheter, or cystoscope. The deployment instrument 402 may be a commercially available device or a device specially adapted for the present drug delivery devices. FIG. 4B illustrates the insertion of the device 400 into the bladder, wherein the adult male anatomy is shown by way of example. The deployment instrument 402 is inserted through the urethra to the bladder, and the device 400 may be passed from/through the deployment instrument 402, driven by a stylet or a flow of lubricant or a combination thereof until the device 400 exits into the bladder, and as shown is in a retention shape.

From the studies described in the Examples below, it has surprisingly been discovered that device embodiments with extremely small release apertures, or orifices, are preferable, and that device embodiments that release drug without a predefined orifice are more preferable. This is because it was observed that these embodiments can be effective to eliminate, or at least substantially reduce the incidences of urothelial lesions, as compared to device embodiments utilizing relative larger release orifices. Without being bound by any theory, it is believed that the larger orifice devices enable the formation of local high drug concentrations of gemcitabine at the urothelial tissue surface in the area adjacent to the release apertures of the device, and that these local tissue areas can be damaged as a result. In contrast, such local high drug concentrations are less likely to occur with device systems utilizing release mechanisms having no predefined orifice or having very small release orifices. Examples of such suitable "no-orifice" release systems are described in PCT Patent Application Publication No. WO 2014/144066 (TB 130) and U.S. Patent Application Publication No. 2014/0276636 (TB 134), which are incorporated herein by reference.

In some embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. For example, the drug may be solubilized upon contact with urine in cases in which the device is implanted in the bladder.

In various embodiments, the intravesical device may release the drug continuously or intermittently to achieve a concentration of the drug in the bladder that produces a sustained, therapeutically effective concentration of the drug in the bladder over a period from 1 hour to 1 month, for example from 2 hours to 2 weeks, from 6 hours to 1 week, from 24 hours to 72 hours, etc. In certain embodiments, the intravesical device may release the gemcitabine in an amount of from 1 mg/day to 1000 mg/day, for example from 20 mg/day to 300 mg/day or from 25 mg/day to 300 mg/day. In certain embodiments, these release rates are provided over a treatment period from 14 days to 21 days.

In one embodiment, the device includes a housing having a release orifice in communication with the drug reservoir in which the gemcitabine is contained, and the drug reservoir further includes a viscosity enhancing agent, an osmotic agent, or a combination of a viscosity enhancing agent and an osmotic agent. In one variation, the gemcitabine is provided in a first region comprising one or more tablets and the osmotic agent and/or viscosity enhancing agent is/are provided in a second region comprising one or more tablets, wherein the first and second regions are discrete spaces within the drug reservoir. The first and second regions may be within a lumen of an annular housing, such as a silicone tube.

Figure 5A:
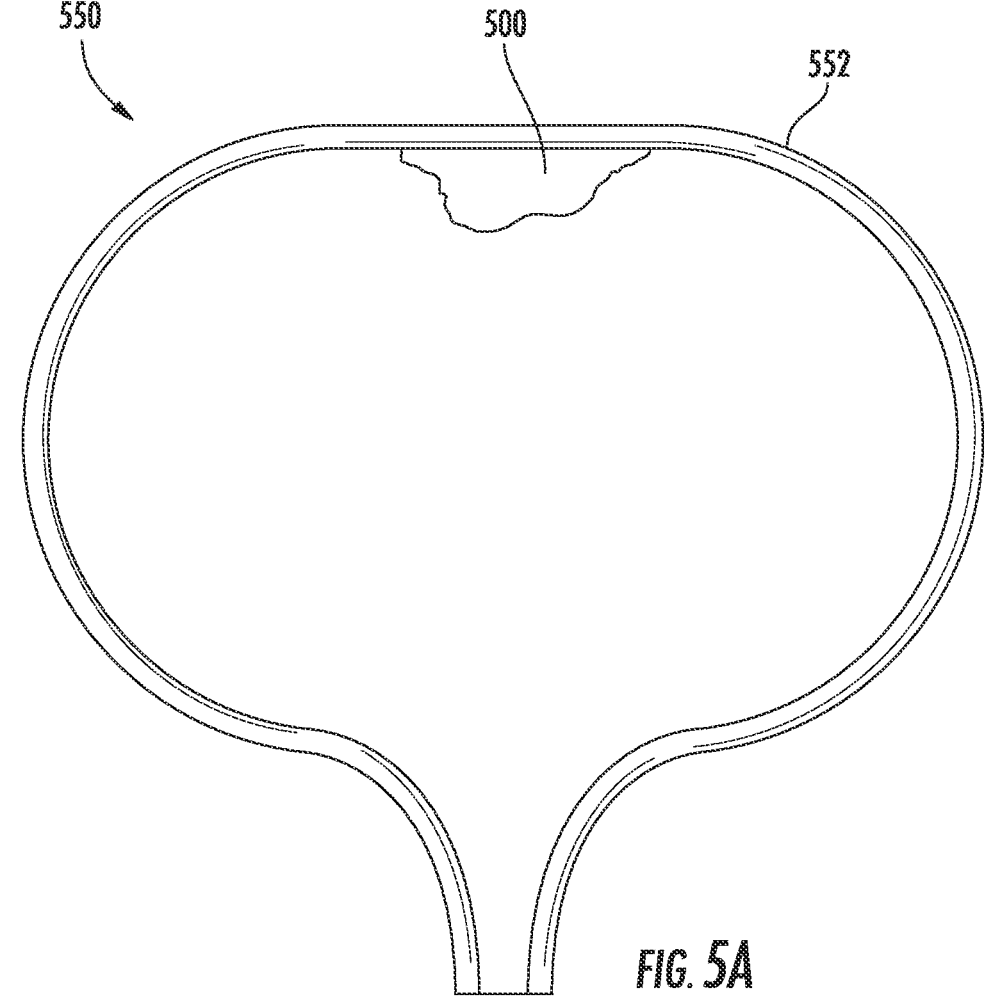
FIG. 5A illustrates a material applied to the inner surface of the bladder wall for local administration of gemcitabine as described herein.

In another embodiment, a coating substance may be intravesically applied to the bladder wall (e.g., to an area of the urothelium inside the urinary bladder), wherein the coating substance includes the gemcitabine or other drug and one or more excipient materials that promote adherance of the coating substance to the bladder wall and provides continuous controlled release of the drug over the treatment period. The coating substance may be a mucoadhesive formulation, such as gels, ointments, creams, pastes, films, emulsion gels, tablets, polymers, or a combination thereof. Mucoadhesive formulation polymers may include hydrogels or hydrophilic polymers, polycarbophil (i.e. Carbopols, etc.), chitosan, polyvinylpyrrolidone (PVP), lectin, polyethyleneglycolated polymers, celluloses, or a combination thereof. Suitable celluloses include methyl cellulose (MC), carboxymethyl cellulose (CMC), hydroxypropyl cellulose (HPC), or combinations thereof. The coating substance may include a permeation enhancer. Non-limiting examples of permeation enhancers include dimethyl sulfoxide (DMSO), sodium carboxymethyl cellulose (NaCMC), lipids, surfactants, or combinations thereof. As shown in FIG. 5A, a coating substance 500 may be deployed in the bladder 550 so that the coating substance 500 engages the bladder wall 552.

Figure 5B:
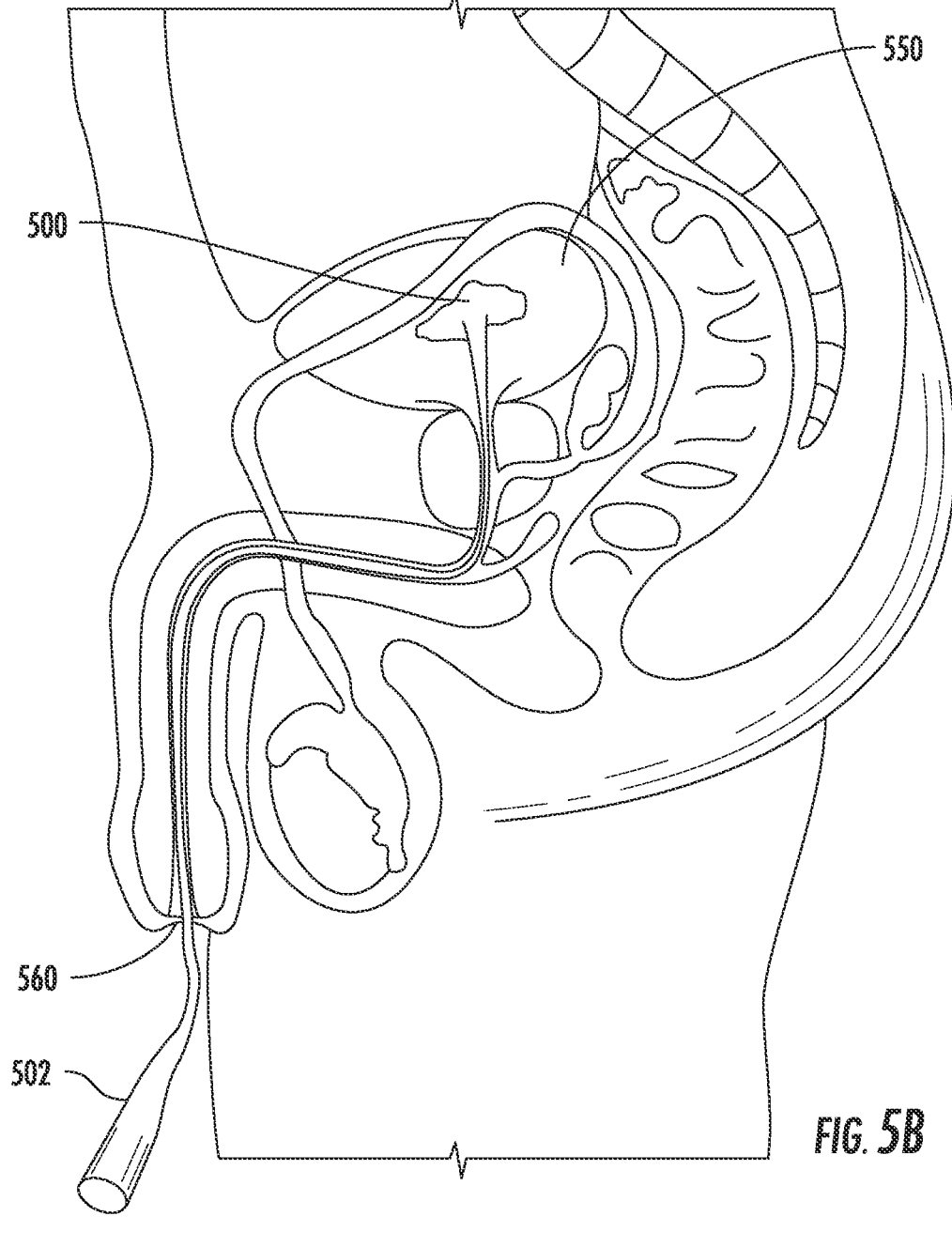
FIG. 5B illustrates a method of applying a coating material onto to the inner surface of the bladder wall for local administration of gemcitabine as described herein.

The coating substance may be deployed in the bladder using a deployment instrument. FIG. 5B is a sagittal view of a male genitourinary system, illustrating a coating substance 500 being deployed through a deployment instrument 502 into an implantation site. By way of example, the male anatomy is shown and the implantation site is shown as the bladder 550. The coating substance 500 may be an embodiment of one of the coating substances described herein. The deployment instrument 502 may be any device designed to navigate natural lumens of the body to reach the intended implantation site. For deployment in the bladder 550, the deployment instrument 502 is sized and shaped for passing through a urethra 560 of a patient to a bladder 550 as shown.

Figure 6:
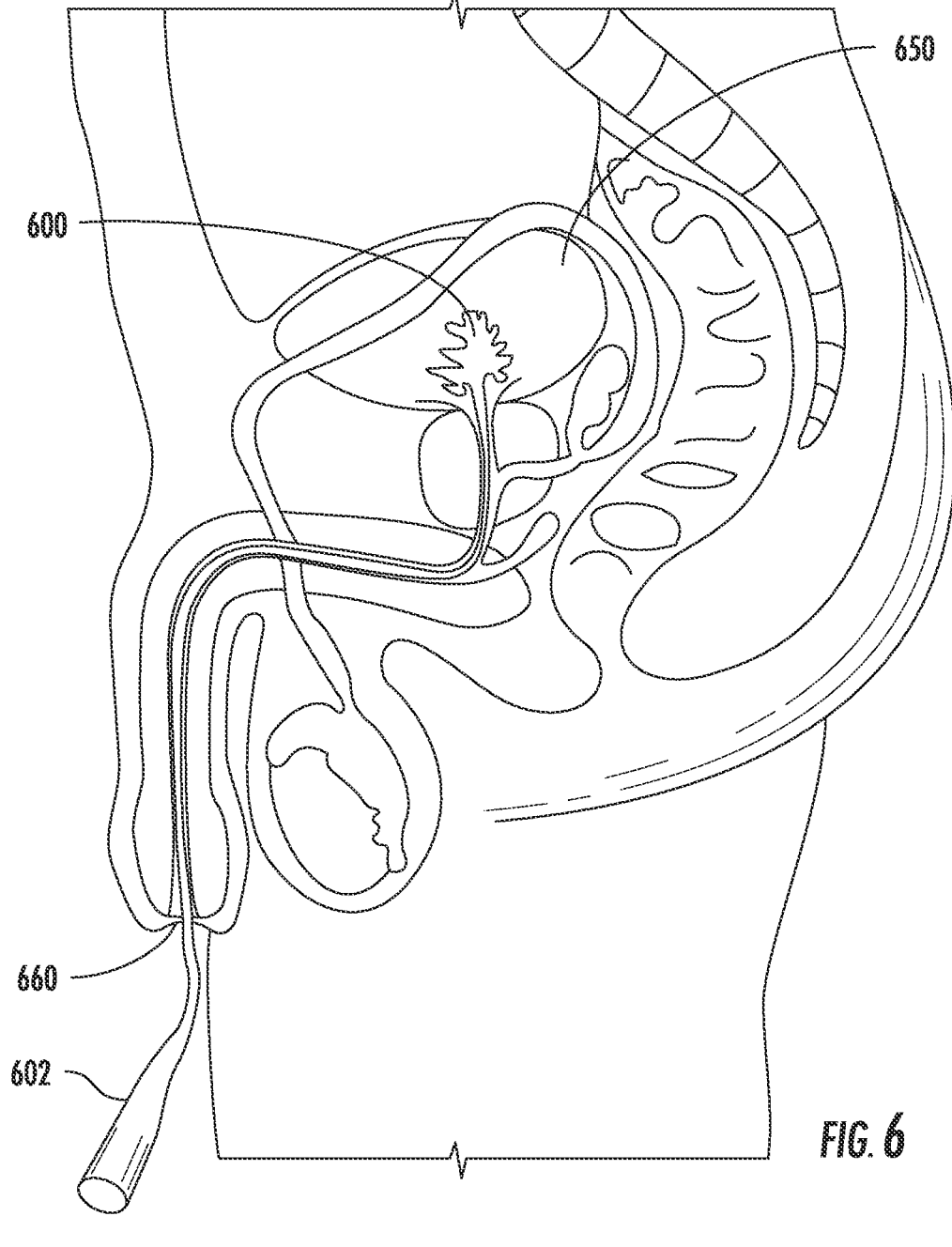
FIG. 6 illustrates a method of applying a liquid drug or drug formulation into the bladder.

The deployment instrument 502 may be a known device, such as a catheter or cystoscope, or a specially designed device. The deployment instrument 502 is used to deploy the coating substance 500 into the body and is subsequently removed from the body, leaving the coating substance 500 wholly implanted in the body. Once so implanted, the coating substance 500 may release drug into the body for an extended period. A comparable procedure can be used to deploy any of the devices or drugs described herein into other parts of the body through other natural lumens. For example, as shown in FIG. 6, a deployment instrument 602 can be used to deploy a liquid drug or drug formulation 600 into the bladder 650 by passing the deployment instrument 602 through a urethra 660.

In one embodiment, a second therapeutic agent is administered to the patient. The second agent may be administered simultaneously, sequentially, or in an overlapping manner, with respect to the administration of the gemcitabine. The second therapeutic agent may be administered intravesically. The methods and systems described herein may be used to administer the second therapeutic agent intravesically. The second therapeutic agent may include a cytotoxic agent, an analgesic agent, an anti-inflammatory agent, or a combination thereof. The second agent may function by a mechanism of action different from the gemcitabine, and/or may function synergistically with the gemcitabine. In one embodiment, the second therapeutic agent prevents, treats, or ameliorates cystitis of the bladder. In still another embodiment, the gemcitabine is used as a chemoimmunotherapeutic first (e.g., during a first week following TURBT) with bacillus Calmette-Guérin (BCG) being administered periodically for a follow-on period thereafter. See, e.g., Cho et al., *J. Int'l Med. Res.* 37:1823-30 (2009).

In various embodiments, the intravesical administration of gemcitabine to the patient can be conducted before TURBT, after TURBT, both before and after TURBT, or without TURBT.

In one embodiment, the intravesical gemcitabine is used in non-muscular invasive bladder cancer (NMIBC) treatment. In another embodiment the intravesical gemcitabine is used in BCG refractory NMIBC. In still another embodiment, it is used in a repeat dose fashion with an induction period followed by a series of maintenance doses, e.g., one-week treatments once a month for three months, followed by a one-week maintenance dose once every three months as appropriate.

The terms "patient" or "subject" as used herein refers to humans or other mammals, such as in veterinary, livestock, and clinic study applications. In a particular embodiment, the patient or subject is an adult human. In other embodiments, the patient or subject includes cows, dogs, cats, goats, sheep, and pigs.

The present invention may be further understood with reference to the following non-limiting examples.

Example 1: Gemcitabine Prostate Uptake from Bladder

A study was conducted on male Sprague Dawley rats administering $^{14}C$ gemcitabine by intra-urinary bladder cannula, over a 6- or 24-hour continuous perfusion, or by a single IV bolus. The 6- and 24-hour continuous perfusions perfused 6.9 and 26.6 mg, respectively, of gemcitabine into the bladder. The single IV bolus included 5.0 mg of gemcitabine.

Figure 7:
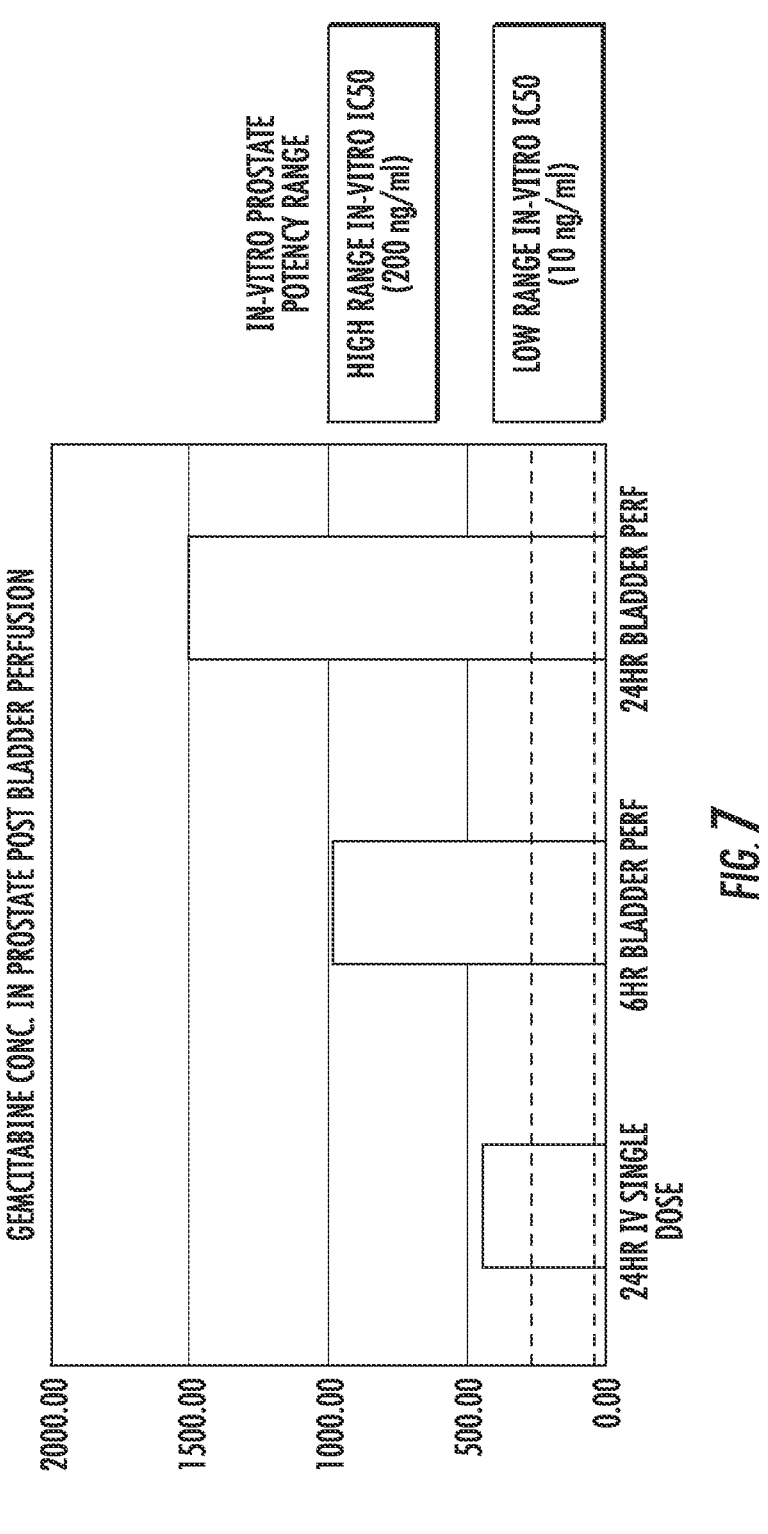
FIG. 7 illustrates the concentration of gemcitabine in the prostate after bladder perfusion and intravenous administration.
Figure 8:
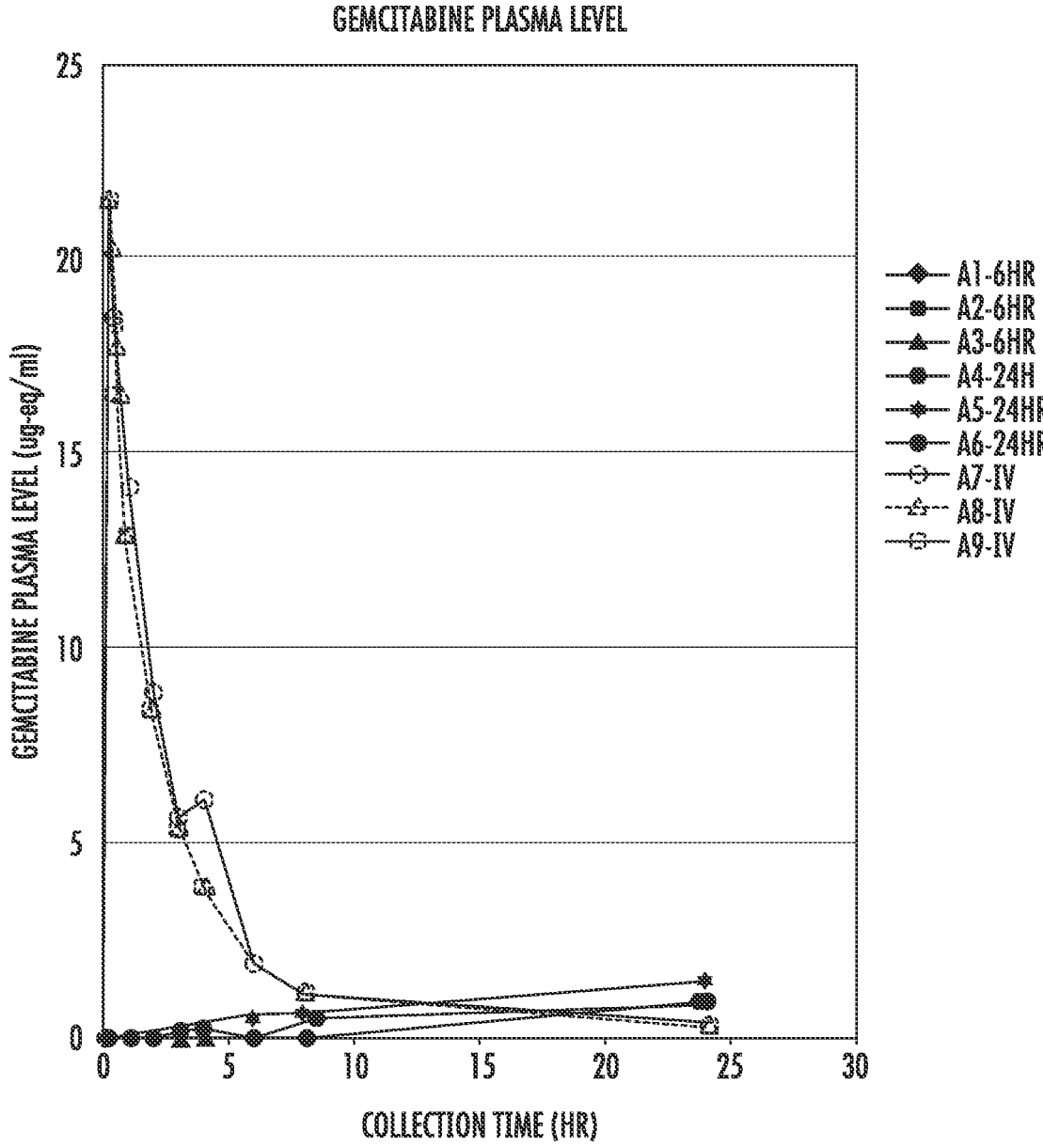
FIG. 8 illustrates the plasma levels of gemcitabine after bladder perfusion and intravenous administration.
Figure 9:
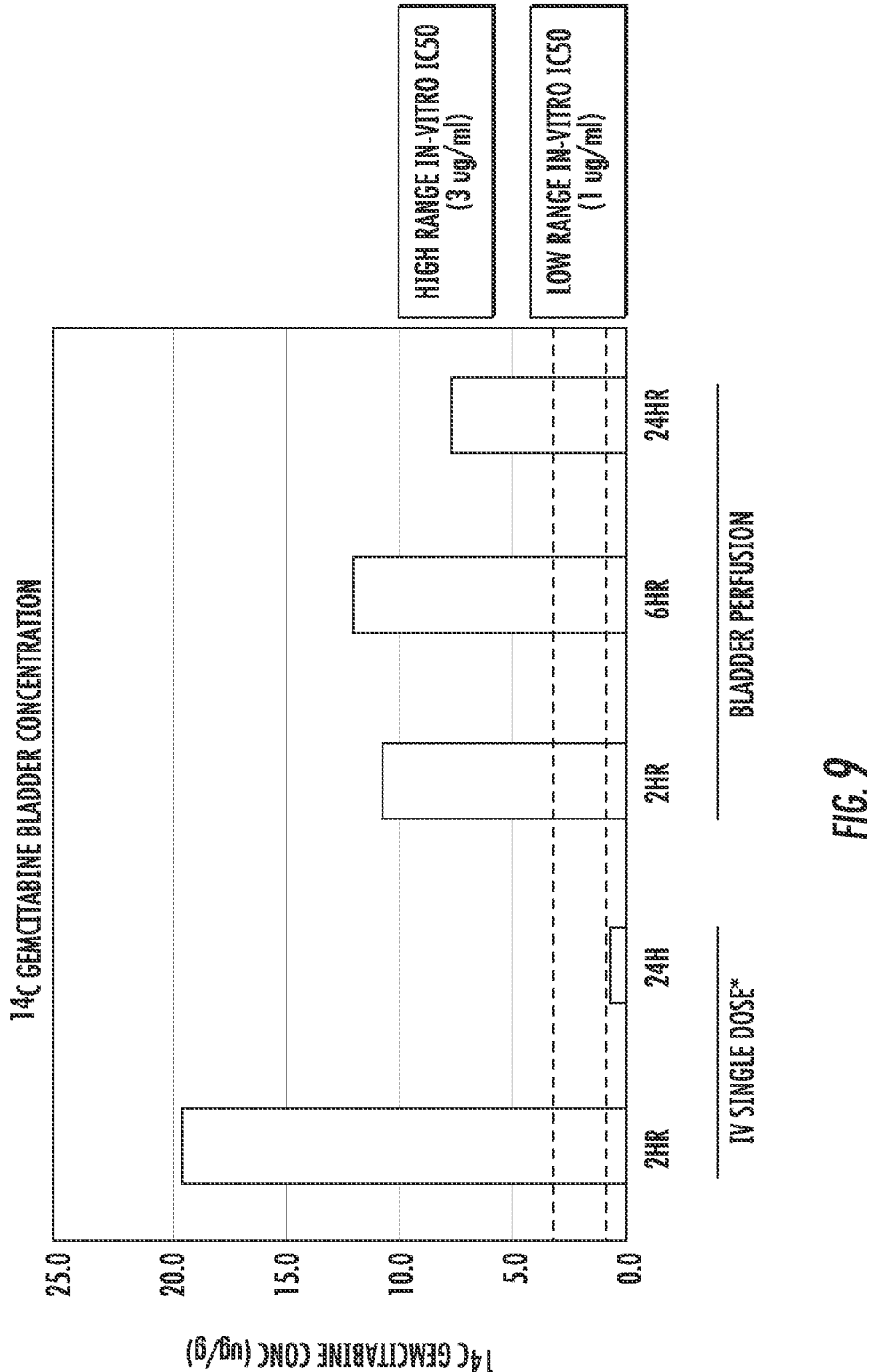
FIG. 9 illustrates $^{14}$C gemcitabine concentration in the bladder after bladder perfusion and intravenous administration.
Figure 14:
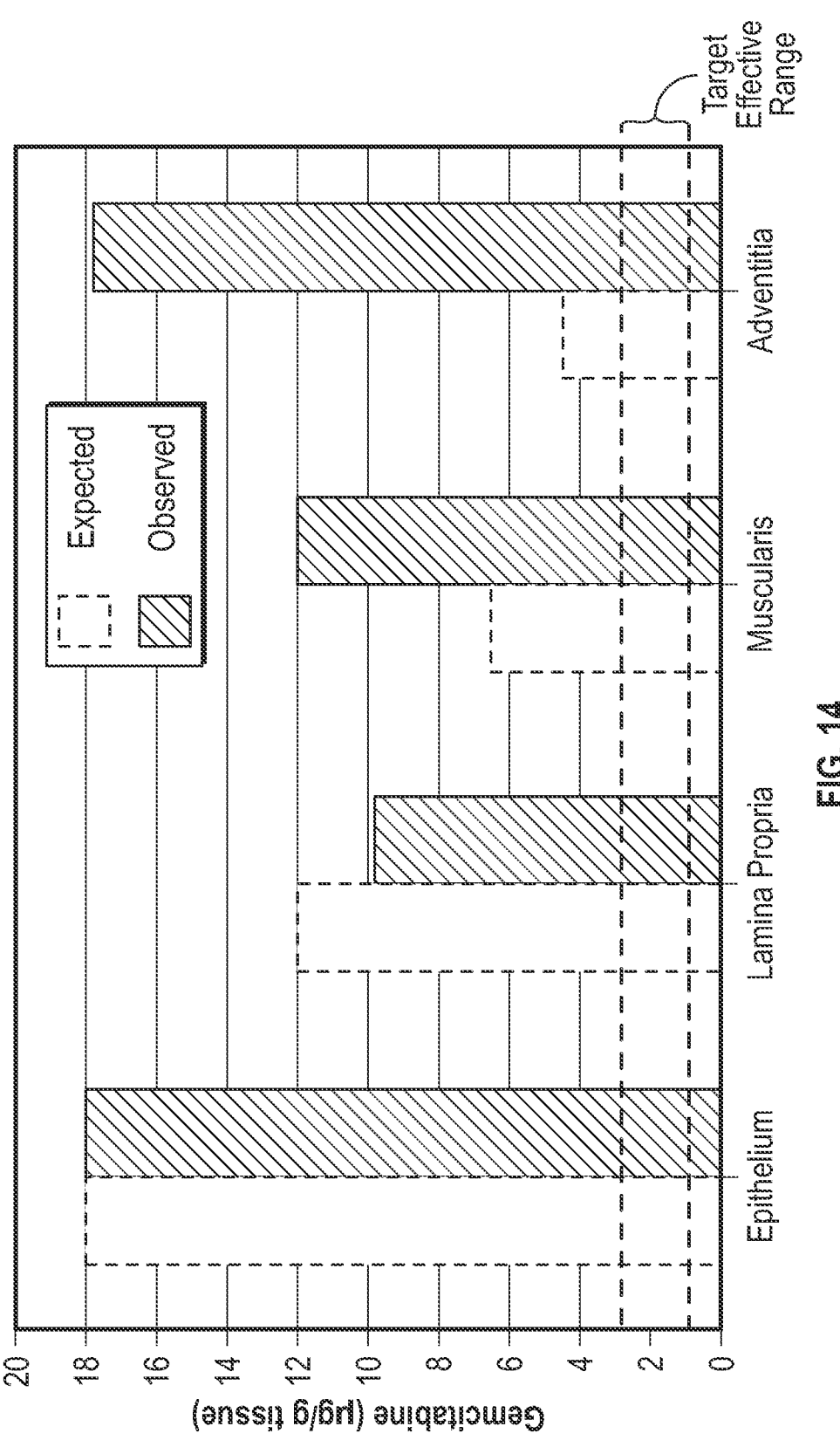

Blood (FIG. 8), urine, and tissue samples (e.g., bladder, prostate) (FIGS. 7 and 9) were collected and analyzed for gemcitabine content. The results are illustrated in FIGS. 7-9. The results show that sustained gemcitabine urine concentrations have been found to produce significant gemcitabine levels in bladder tissue, which are at or exceed therapeutic concentrations based on in vitro bladder cancer cell experiments. The gemcitabine levels in the bladder are shown in FIG. 9, which also depicts a significantly lower concentration of gemcitabine in the bladder 24 hours after a clinically relevant IV dose. The gemcitabine levels observed for each of the bladder epithelium, lamina propria, muscularis, and adventitia are shown in FIG. 14, which also illustrates a target effective range for the gemcitabine tissue concentration.

Example 2: Gemcitabine Study in Large Mixed Breed Hounds

Two gemcitabine release systems (devices as shown in FIGS. 1A-1B) designed to release therapeutic levels (4 mg/day and 40 mg/day) into the urine were screened. The devices used either laser-drilled orifices or punched orifices for release of the gemcitabine. The systems tested were compared to intravesical instillations which were designed to mimic the standard intravesical doses used clinically. The test animals were large mixed breed hounds, with N=3 for each group.

Each system in vitro exhibited different release rates of gemcitabine. In vivo, one system yielded very low urine and tissue concentrations but was well tolerated by the test animal. The other system produced target urine concentration levels but was poorly tolerated by the test animal. Urine profiles were also variable and the duration of drug release was unacceptably short. It was also observed that intravesical administration produced significant urothelial lesions consistent with the symptoms reported in the literature.

In sum, this study demonstrated that the device/tablet formulation design impacts both gemcitabine urine concentrations over time and bladder tolerability.

Example 3: Gemcitabine Bladder Perfusion Study in Minipigs

Varying concentrations of gemcitabine were perfused into pigs for 7 days, N=5 (2 males and 3 females per treatment group). The perfusion animals were dosed at concentrations selected to bracket the target doses for bladder cancer in humans. For comparison, a gemcitabine releasing device (as shown in FIGS. 1A-1B) with large bore end caps (restraining plugs with a large aperture therethrough for drug release) with an intermediate in vitro release rate was deployed in a separate group of animals. All perfusion groups tolerated gemcitabine well, including the highest perfusion dose. In contrast, the gemcitabine-releasing devices produced intermediate urine concentrations but were not well tolerated.

Example 4: Modular Device Releasing Gemcitabine by Permeation System

Figure 10A:
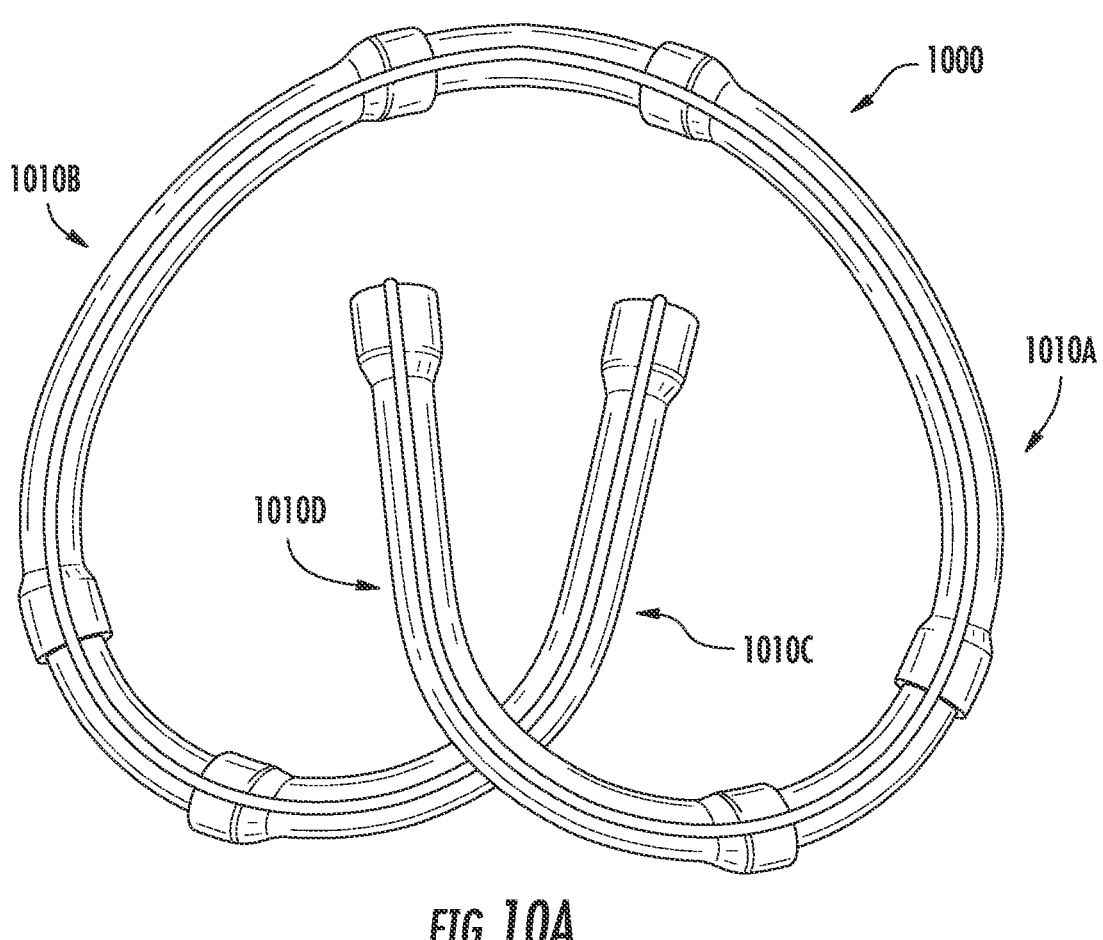
FIGS. 10A-C illustrate one embodiment of an intravesical drug delivery device for releasing gemcitabine via permeation disks.
Figure 10B:
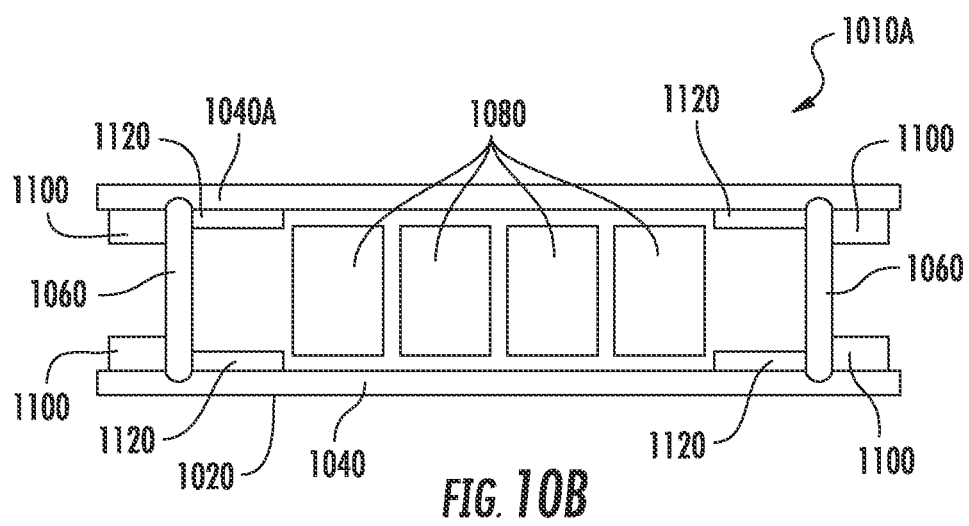
Figure 10C:
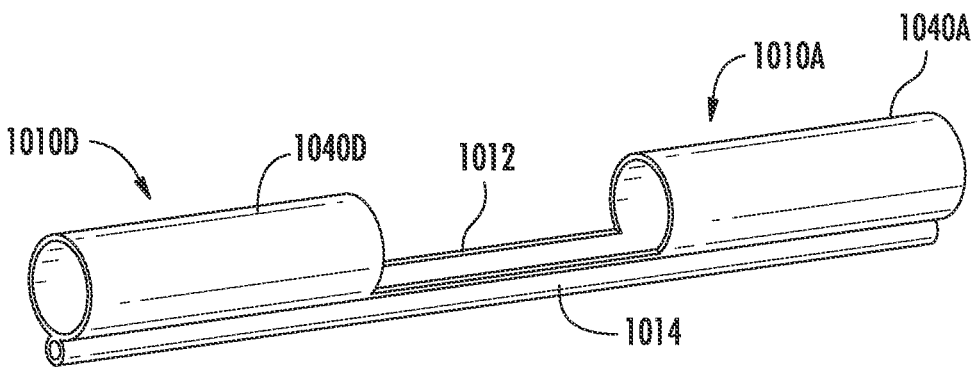

Gemcitabine HCl was tested in a four-module device 1000, which is illustrated in FIGS. 10A-C. FIG. 10A shows that device 1000 includes four drug reservoir modules 1010A, 1010B, 1010C, and 1010D. For clarity, FIG. 10C shows only the housing portion of the device (with other components omitted) and only for drug reservoir modules 1010A and 1010D. FIG. 10C illustrates how the reservoir sidewalls 1040A and 1040D of drug reservoir modules 1010A and 1010D, respectively are integrally connected by wall segment 1012 and retention frame lumen 1014. The reservoir sidewalls 1040A and 1040D, as well as wall segment 1012, and retention frame lumen 1014 were formed by cutting a segment out of a dual-lumen silicone tube. (The four-module device was made by cutting three, spaced segments out of the dual lumen silicone tube.) Each drug reservoir module was comprised of silicone tube made of MED-4750 (Nusil) with the dimensions of 2.64 mm ID and 0.20 mm wall thickness. The silicone tube included a retention frame lumen having a 0.51 mm ID and 0.20 mm wall thickness. A nitinol retention frame was inserted into the retention frame lumen 1014. FIG. 10B illustrates the structure of drug reservoir module 1010A, including the disks 1060 through which solubilized drug was released by diffusion. (The other three drug reservoir modules were identical in construction to module 1010A.) Disk 1060 is stabilized within the lumen of the cylindrical tube sidewalls 1040A by sandwiching the disk 1060 between outer washer 1100 and inner washer 1120. Each disk 1060 was made of HP-93A-100 (Tecophilic® Thermoplastic Polyurethanes), and the dimensions of each disk 1060 were approximately 0.5 mm thickness and 3.0 mm OD. The OD (3.0 mm) of the disk was larger than the silicone tube ID (2.64 mm), and so the disk was frictionally fit in the silicone tube. The inner and outer silicone washers 1120, 1100 were made of MED-4780 (Nusil), and located next to disks 1060 with silicone adhesive applied around the washers 1120, 1100 to fix the washers in the silicone tube 1040A. The silicone outer washer 1100 had the dimensions of ID, OD, and the length of approximately 2.5 mm, 3.2 mm, and 2 mm, respectively, and the silicone inner washer 1120 had the dimensions of ID, OD, and the length of approximately 1.58 mm, 2.77 mm, and 2 mm, respectively.

Multiple drug tablets 1080 with 2.6 mm OD were loaded into the silicone tube 1040A before closing off both ends of the reservoir with disk 1060 and inner and outer washers 1120 and 1100. The tablet formulation was 90% gemcitabine HCl, 5% PVP, 2.5% Neusilin, and 2.5% magnesium stearate. The total mass of the tablets loaded in each four-module device was approximately 800 mg.

Figure 11:
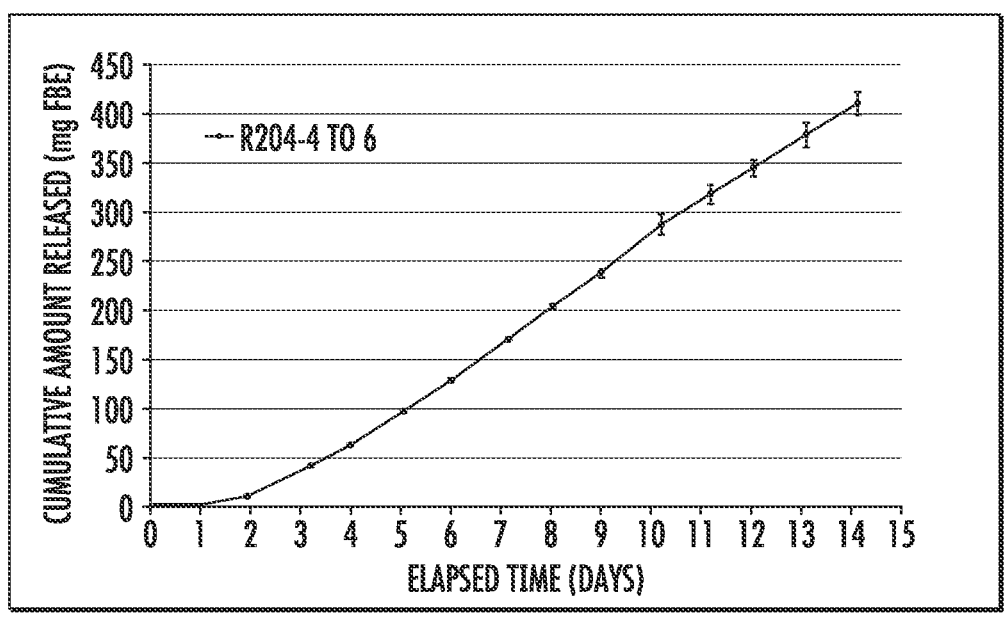
FIGS. 11-12 are graphs showing in cumulative amounts of gemcitabine released in vitro from the devices shown in FIGS. 10A-C.
Figure 12:
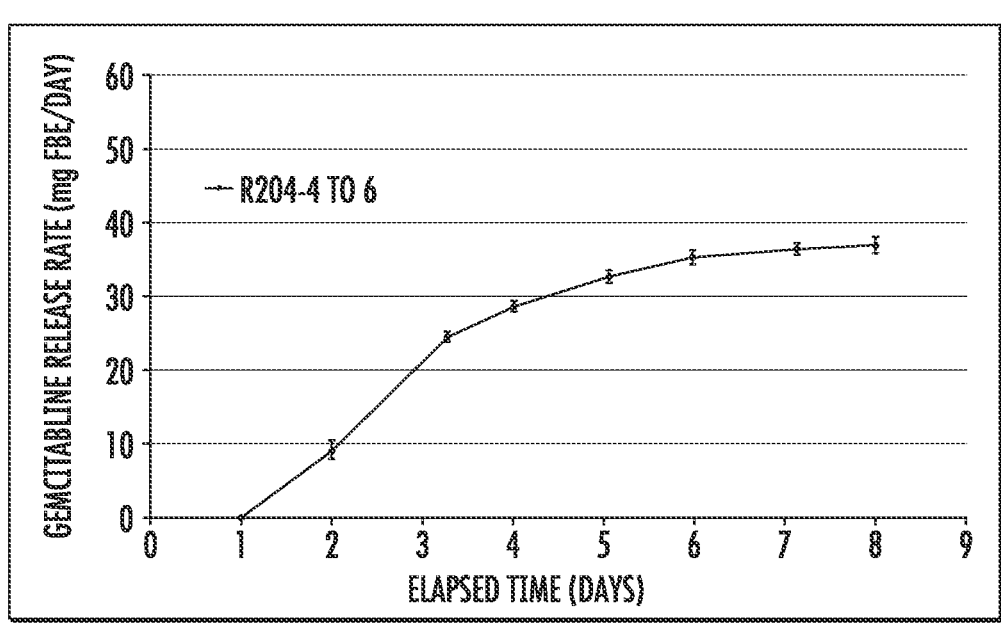

In vitro release experiment with three units (R204-4 to 6) was performed at 37° C. The release medium was deionized water, and time point samples were collected. Gemcitabine release was controlled by diffusion through the Tecophilic disks. The cumulative amount and release rate in free base equivalent (FBE) are shown in FIG. 11 and FIG. 12, respectively. Each error bar is standard deviation around the mean (n=3). Some error bars are smaller than symbols.

Figure 13:
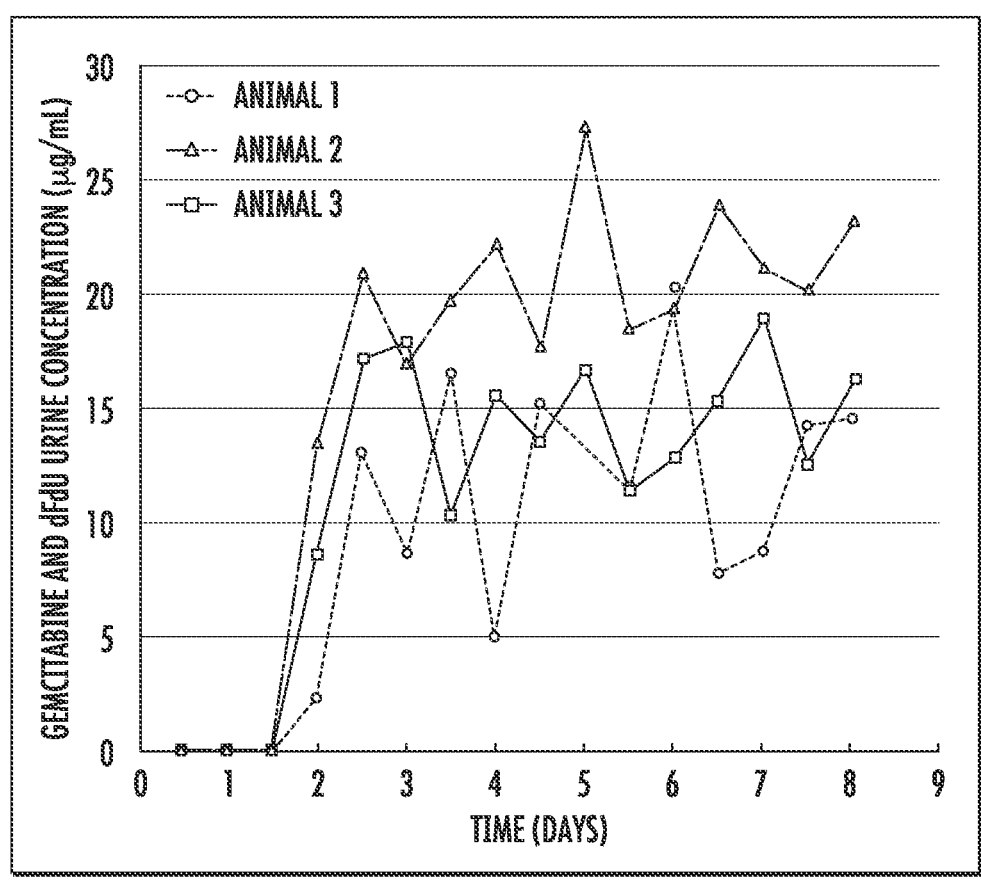
FIGS. 13-14 are graphs showing in urine concentrations of gemcitabine, dFdU, and the combination thereof, respectively, from an animal study.

The devices with the same design were tested in vivo with three Göttingen minipigs. Each device was inserted into the bladder of each animal through the urethra non-surgically by cystoscope. The urine concentration of gemcitabine and 2',2'-difluoro-2'-deoxyuridine (dFdU) was measured over an 8-day period. After the 8-day study, each device was removed through the urethra non-surgically by cystoscope and forceps. The urine concentration of the combined gemcitabine and dFdU is shown in FIG. 13.

Example 5: Gemcitabine Delivery Device Screen Studies in Minipigs

A series of prototype screening studies were undertaken to refine the drug delivery system design based on the intrinsic tolerability of gemcitabine discovered in the mini pig perfusion study described above. In this study, three prototype devices were designed to release therapeutic levels of gemcitabine into the urine. Two devices were of the FIGS.

1A-1B design (with large bore end caps or laser-drilled orifices for drug release) and one device was of the FIGS. 10A-10C design (drug permeable disks for drug release). Three studies were completed, each study tested a single prototype design in three minipigs in which blood and urine samples were intensively collected over a 7-day period.

The devices of the FIGS. 1A-1B design having large bore end caps for drug release were found to consistently produce urothelial lesions in the animal. However, devices of the FIGS. 1A-1B design having a laser-drilled orifice in which a viscosity enhancing agent was included with the gemcitabine were found to reduce the incidences of urothelial lesions. The no-orifice devices of the FIGS. 10A-10C design were found to completely eliminate the incidences of urothelial lesions. Such a design is believed to prevent transient high local concentrations of the gemcitabine (at the tissue surfaces adjacent to the device's drug release apertures) which are believed to contribute to the incidences of urothelial lesions.

Example 6: Gemcitabine Delivery Device Screen Studies in Minipigs

In this study, osmotic prototype devices were designed to release therapeutic levels of gemcitabine into the urine. The devices were configured to use tablets of gemcitabine and tablets of osmotic agent positioned in separate positions within the drug reservoir, as described generally in PCT WO 2015/026813, which is incorporated in pertinent part herein. A first subset of the devices each included a silicone tube having a 75-micron laser-drilled orifice in a region centrally located between the ends of the tube for drug release. The lumen of the tube was loaded with tablets of a mixture of gemcitabine and urea in the central region about the release orifice and with tablets of urea/Lubritab in the end regions of the lumen. A second subset of the devices each included a silicone tube having a 150-micron laser-drilled orifice in a region centrally located between the ends of the tube for drug release. The lumen of the tube was loaded with tablets of a mixture of gemcitabine and urea in the central region about the release orifice and with tablets of urea/PEO in the end regions of the lumen. The devices were tested in vivo in minipigs and in vitro, measuring cumulative and average gemcitabine released over 7 days. Gemcitabine release rates were approximately 120 mg over 7 days from the 75 micron orifice device and approximately 140 mg over 7 days from the 150 micron orifice device. Variations in urine concentration with time were observed to be modestly less using the urea/PEO formulation when compared with the urea/Lubritab formulation. The viscosity of solubilized drug solution in the device lumen therefore may be a factor in controlling drug release.

Conclusions from the Examples

Literature studies providing target concentrations—in vitro concentrations across tumor cell lines—typically have IC50 values ranging between 0.5 and 3.0 µg/g (microgram per gram) for responsive cell lines (see Jeon et al., *J. Urol.* 186(5):2084-93 (2011)). The literature also suggests that high urine concentrations (e.g., 2000 mg in up to 50 mL) are required for efficacy, but that intravesical instillations to achieve such concentrations are associated with issues of safety and tolerability, systemic toxicity, and lower urinary tract symptoms (LUTS) (see Cattel et al., *Annals Oncol.* 17(Supp 5): v142-47 (2006)).

However, from the studies described in the foregoing Examples, concentrations of gemcitabine in urine needed to achieve these therapeutic tissue concentrations have been determined, and found to be tolerated by the urothelium. That is, high intravesical urine concentrations are not required. In particular, it has been discovered that an intravesical system delivering $1/100^{th}$ of those levels (e.g., 20 mg in up to 50 mL) can be effective.

Also, it has been discovered by that prolonged intravesical delivery of gemcitabine can be carried out without damage to the urothelium, in contrast to what the literature taught regarding intravenous perfusion of gemcitabine.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A method for treating non-muscle invasive bladder cancer (NMIBC) in a human patient, comprising:
   administering from 10 mg/day to 50 mg/day of gemcitabine free base equipment (FBE) continuously to the bladder of the human patient over a treatment period of 21 days by deploying into the human patient's bladder an intravesical drug delivery device which comprises the gemcitabine and urea;
   wherein the intravesical drug delivery device comprises a housing that is elastically deformable between a retention shape configured to retain the intravesical drug delivery device in the bladder and a deployment shape for passage of the intravesical drug delivery device through a urethra,
   wherein the housing comprises a predefined release aperture and a drug reservoir, the drug reservoir having a first region and a second region that is a distinct space from the first region,
   wherein the gemcitabine is located in the first region in the form of one or more gemcitabine minitablets, and wherein the urea is located in the second region in the form of one or more urea minitablets;
   wherein the treatment does not comprise a therapeutic agent other than gemcitabine;
   releasing the gemcitabine from the predefined release aperture by osmotic pressure generated by the urea minitablets and into urine in the human patient's bladder,
   and
   wherein the human patient has not responded to Bacile Calmette-Guerin (BCG) treatment or wherein the human patient experienced adverse effects leading to discontinuation of BCG treatment.

2. The method of claim 1, wherein the housing contains and controls the release of the gemcitabine.

3. The method of claim 2, wherein the predefined release aperture is in communication with the drug reservoir.

4. The method of claim 1, wherein the intravesical drug delivery device is deployed into the human patient's bladder after a transurethral resection of bladder tumors (TURBT).

5. The method of claim 1, wherein the intravesical drug delivery device is deployed into the human patient's bladder before a transurethral resection of bladder tumors (TURBT).

* * * * *